US012619852B2

(12) United States Patent
    Stokes

(10) Patent No.: US 12,619,852 B2
(45) Date of Patent: May 5, 2026

(54) METHOD AND SYSTEM FOR SIMULATING, PREDICTING, INTERPRETING, COMPARING, OR VISUALIZING COMPLEX DATA

(71) Applicant: OHUKU LLC, Honolulu, HI (US)

(72) Inventor: Alexander J. Stokes, Honolulu, HI (US)

(73) Assignee: OHUKU LLC, Honolulu, HI (US)

( * ) Notice: Subject to any disclaimer, the term of this patent is extended or adjusted under 35 U.S.C. 154(b) by 878 days.

(21) Appl. No.: 16/461,763

(22) PCT Filed: Jan. 27, 2018

(86) PCT No.: PCT/US2018/015620
    § 371 (c)(1),
    (2) Date: May 16, 2019

(87) PCT Pub. No.: WO2018/140839
    PCT Pub. Date: Aug. 2, 2018

(65) Prior Publication Data
    US 2019/0362216 A1      Nov. 28, 2019

Related U.S. Application Data

(60) Provisional application No. 62/451,412, filed on Jan. 27, 2017.

(51) Int. Cl.
    *G06N 3/004*      (2023.01)
    *G06F 3/01*       (2006.01)
            (Continued)

(52) U.S. Cl.
    CPC ............. *G06N 3/004* (2013.01); *G06F 3/011* (2013.01); *G06F 3/016* (2013.01); *G06Q 10/06* (2013.01); *G06Q 10/0674* (2025.08); *G16B 5/00* (2019.02)

(58) Field of Classification Search
    CPC ........ G06N 3/004; G06N 3/006; G06N 3/008; G06F 30/20; G06F 3/011; G06F 3/016;
            (Continued)

(56) References Cited

U.S. PATENT DOCUMENTS 5,907,487 A      5/1999   Rosenberg
6,995,768 B2 *   2/2006   Jou ......................... G06F 9/542
                                                      345/440
            (Continued)

OTHER PUBLICATIONS

Fitz-Rodriguez et al., "Dynamic modeling and simulation of greenhouse environments under several scenarios: A web-based application," Computers and Electronics in Agriculture 70 (2010) 105-116 (Year: 2010).*
            (Continued)

*Primary Examiner* — Miranda M Huang
*Assistant Examiner* — Yao David Huang

(57)      ABSTRACT

A method may include receiving a data stream of complex data and receiving a type of a simulated organic life model and a type of a simulated environment. The method may include selecting a scenario for a simulation, parsing each variable in the data stream to a variable of the simulated organic life model or a variable of the simulated environment, and processing a simulation of the simulated organic life model in the simulated environment. The method may include altering one or more variables of the simulated organic life model based on one or more variables of the simulated environment, producing output data sets containing a continuum of data ranging from the data stream to predicted endpoint values for each data stream variable, and changing the simulated organic life model based on the altered one or more variables of the simulated organic life model.

18 Claims, 21 Drawing Sheets

Example Simulation                     Simulation Processed

Simulated Environment                  Simulated Environment

Extrinsic Variables=Environmental Parameters   Extrinsic Variables=Environmental Parameters
That Can Effect Changes In The Intrinsic       That Can Effect Changes In The Intrinsic
Variables Of The Model                          Variables Of The Model Simulated Organic Life Model            Simulated Organic Life Model Example Extrinsic Variables ~ Better Rain And Sun, Less Wind, Better Soil
Example Extrinsic Variables Changed By The Simulation. ~ Better Growth, Bigger Roots, Bigger Trunk, More Fruit, More Leaves.
Therefore Tree Is "Healthier" Under This Simulation

(51) Int. Cl.

| | | |
|---|---|---|
| *G06Q 10/06* | (2023.01) | |
| *G06Q 10/067* | (2023.01) | |
| *G16B 5/00* | (2019.01) | |

(58) Field of Classification Search
CPC .... G16B 5/00; G06Q 10/067; G06Q 10/0674; G06Q 10/04; G06Q 30/0202
See application file for complete search history.

(56) References Cited

U.S. PATENT DOCUMENTS

| | | | | |
|---|---|---|---|---|
| 8,296,070 | B2 | 10/2012 | Paxson | |
| 8,606,610 | B2 * | 12/2013 | Black | G06Q 10/063 705/7.12 |
| 9,761,036 | B2 * | 9/2017 | Rzeszotarski | G06T 13/80 |
| 2004/0024543 | A1 | 2/2004 | Zhang | |
| 2004/0088116 | A1 * | 5/2004 | Khalil | G16B 40/10 703/11 |
| 2005/0004785 | A1 * | 1/2005 | Temkin | G16B 50/00 703/11 |
| 2005/0187747 | A1 * | 8/2005 | Paxson | G16B 5/00 703/11 |
| 2007/0207846 | A1 * | 9/2007 | Burak | A63F 13/77 463/9 |
| 2009/0099784 | A1 | 4/2009 | Ladd | |
| 2010/0153082 | A1 * | 6/2010 | Newman | G01N 33/5008 703/11 |
| 2010/0285082 | A1 * | 11/2010 | Fernandez | A61B 5/024 506/13 |
| 2012/0173215 | A1 * | 7/2012 | Buchan | G16H 40/20 715/804 |
| 2012/0225414 | A1 * | 9/2012 | Kim | G09B 5/02 434/295 |
| 2014/0114987 | A1 | 4/2014 | Hoeng | |
| 2015/0348066 | A1 * | 12/2015 | Sewak | G06Q 10/063 705/7.31 |
| 2015/0363820 | A1 | 12/2015 | Leitersdorf et al. | |
| 2017/0010671 | A1 * | 1/2017 | Ghaffari Toiserkan | B25J 9/1689 |
| 2017/0075340 | A1 * | 3/2017 | Claeys | G05B 19/4063 |
| 2017/0109496 | A1 * | 4/2017 | Hisada | G16H 50/50 |
| 2017/0140669 | A1 * | 5/2017 | Dey | G06F 1/1694 |
| 2018/0065038 | A1 * | 3/2018 | Margiotta | G06Q 10/0639 |
| 2018/0089893 | A1 * | 3/2018 | Kukis | G02B 27/017 |

OTHER PUBLICATIONS

Tang et al., "An integrated system for 3D tree modeling and growth simulation," Environ Earth Sci (2015) 74:7015-7028 (Year: 2015).*
Raungpaka et al., "Preliminary Results-Nature as Metaphor: Innovative Visualization of Accounting Information with Lotus Plants," ResearchGate paper (Nov. 2012) (Year: 2012).*

* cited by examiner

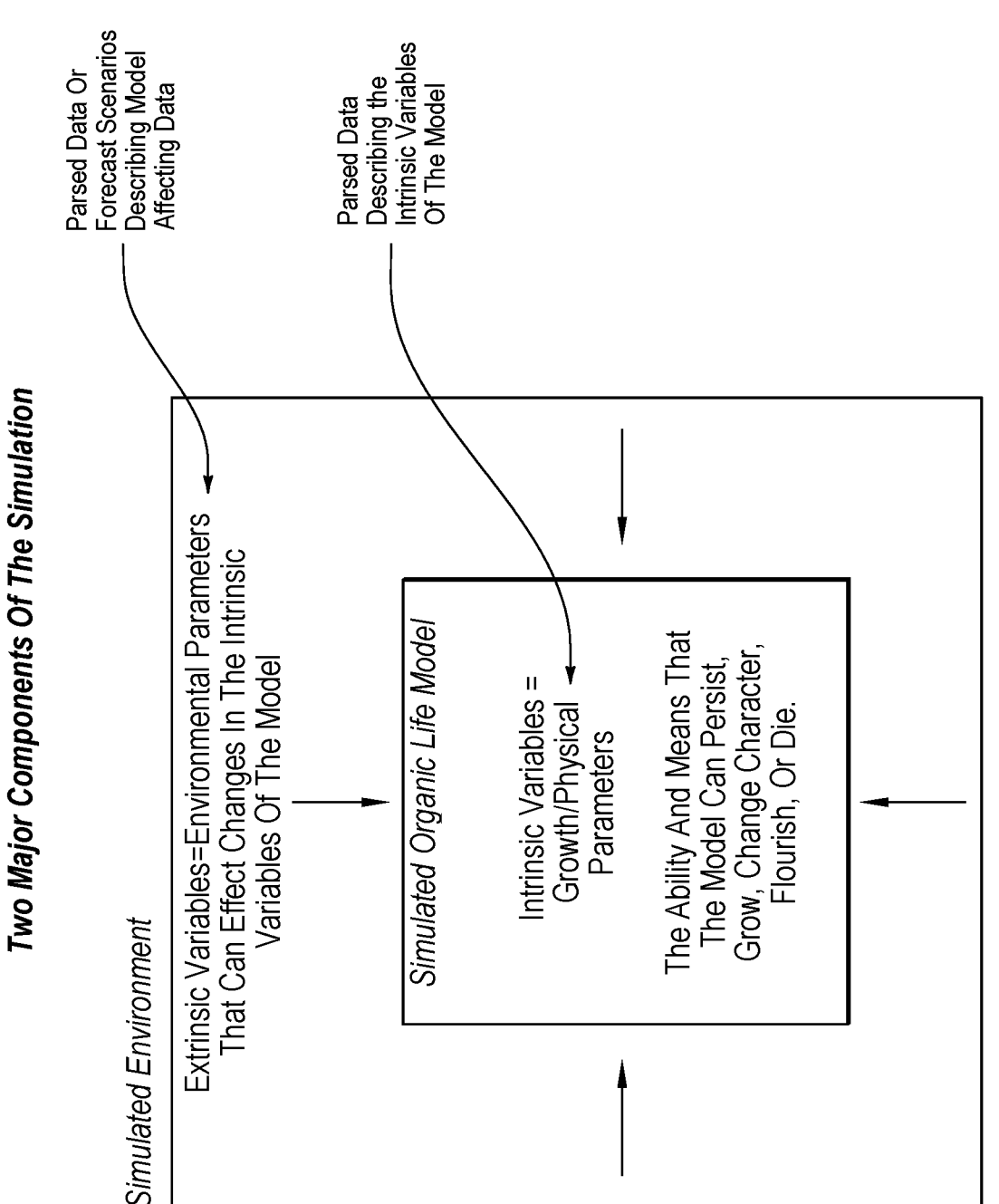

Two Major Components Of The Simulation

Parsed Data Or Forecast Scenarios Describing Model Affecting Data

Parsed Data Describing the Intrinsic Variables Of The Model

*Simulated Environment*

Extrinsic Variables=Environmental Parameters That Can Effect Changes In The Intrinsic Variables Of The Model

*Simulated Organic Life Model*

Intrinsic Variables = Growth/Physical Parameters

The Ability And Means That The Model Can Persist, Grow, Change Character, Flourish, Or Die.

| | A | B | C | D | E | F | G | H |
|---|---|---|---|---|---|---|---|---|
| State 2 - Simulation, Processed With ~ Negative Extrinsic Environment | Deteriorated | Stable | Stable | Deteriorated | Stable | Stable | Deteriorated | Deteriorated |
| | Lost Leaves | Did Not Grow | Did Not Grow | Lost Leaves | Did Not Grow | Did Not Grow | Lost Leaves | Lost Leaves |
| | Did Not Grow | | | Lost All Branches | | | Lost A Few Branches | Lost A Few Branches |
| | | | | Broken Trunk | | | Lost All Fruit | Lost A Few Fruit |
| | | | | Died | | | | |
| State 3 - Simulation, Processed With ~ Positive Extrinsic Environment | Stable | Improved | Improved | Stable | Improved | Stable | Stable | Stable |
| | Did Not Grow | Produced Few Fruit | Grew Much Bigger | Did Not Grow | Grew Bigger | Did Not Grow | Did Not Grow | Did Not Grow |
| | | | Produced More Branches | | Produced More Branches | | | |
| | | | Produced More Leaves | | Produced More Leaves | | | |
| | | | Roots Grew Bigger | | Roots Grew Bigger | | | |

*FIG. 5E*

State 2

State 1

State 3

State 2

State 1

State 1

State 2

State 3

Altering Extrinsic Variables

Applying Rain

Positive Growth Effect

User Interaction

State 2

State 1

*FIG. 7A*

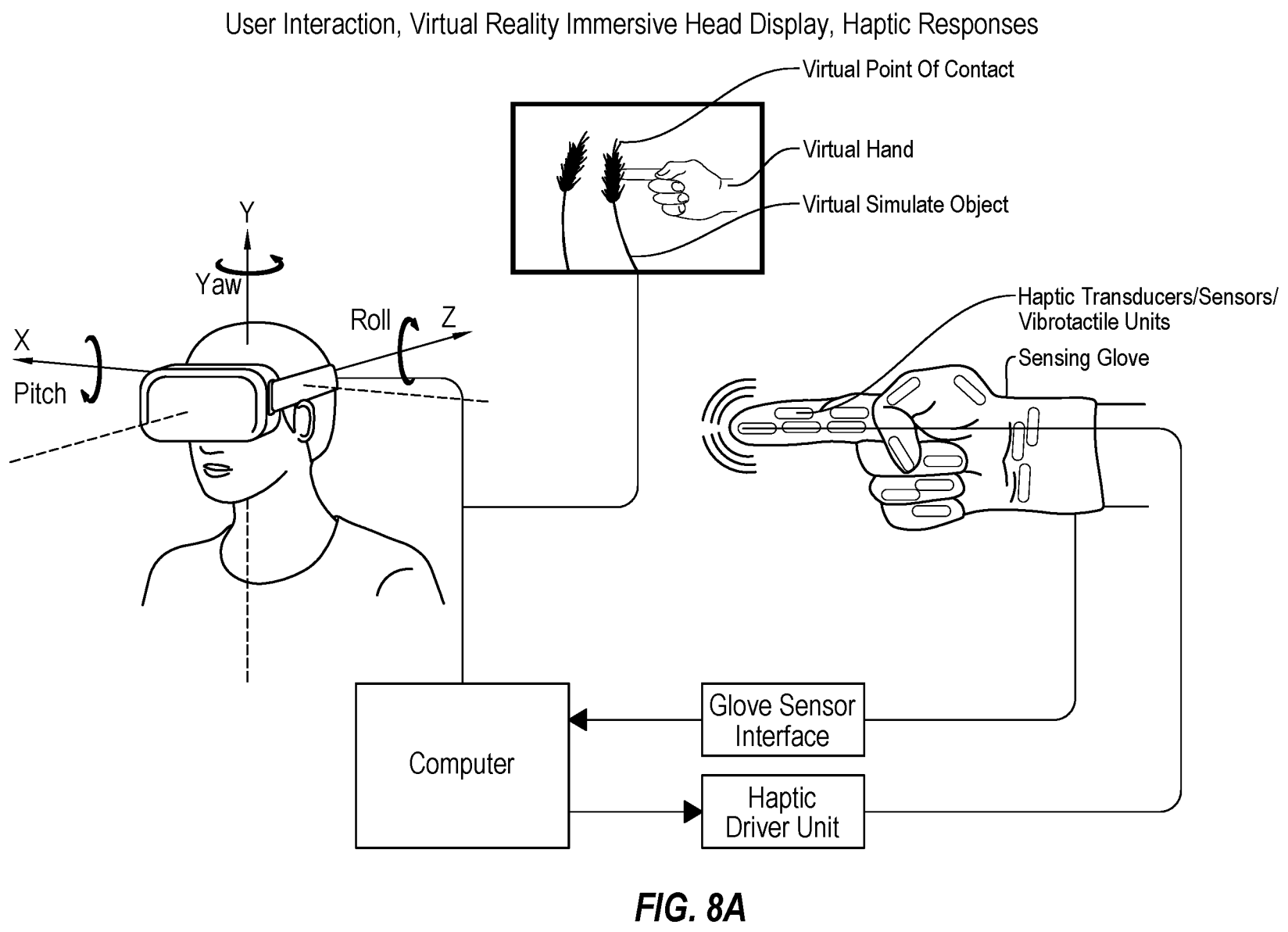

User Interaction, Virtual Reality Immersive Head Display, Haptic Responses

Virtual Point Of Contact

Virtual Hand

Virtual Simulate Object

Haptic Transducers/Sensors/ Vibrotactile Units

Sensing Glove

Glove Sensor Interface

Haptic Driver Unit

Computer

Roll

Z

Y

Yaw

X

Pitch

*FIG. 8A*

User Interaction, Gesture And Movement Sensing

User Interaction, Haptic Sensing

METHOD AND SYSTEM FOR SIMULATING, PREDICTING, INTERPRETING, COMPARING, OR VISUALIZING COMPLEX DATA

FIELD

The application relates generally to a method and system for simulating, predicting, interpreting, comparing, or visualizing complex data

BACKGROUND

Analysis, monitoring, and prediction of complex data can involve the collection and display of large amounts of disparate information from a multitude of sources. This numerical or categorical data is usually viewed as numerous text, graphs, or numerical summaries, by individuals who process, identify data patterns, and then predict future outcomes, based on the type of data and their personal experience in analysis of this data type. Such processes and methodologies may be complex and may require a degree of expertise beyond that of many individuals.

The subject matter claimed herein is not limited to embodiments that solve any disadvantages or that operate only in environments such as those described above. Rather, this background is only provided to illustrate one example technology area where some embodiments described herein may be practiced.

SUMMARY

Embodiments of the present disclosure may include a method of simulating, predicting, comparing, and/or conveying complex data. The method may include receiving a data stream of complex data and receiving a type of a simulated organic life model and a type of a simulated environment. The method may further include selecting a scenario for a simulation and parsing each variable in the data stream to a variable of the simulated organic life model or a variable of the simulated environment. Additionally, the method may include processing a simulation of the simulated organic life model in the simulated environment based on the parsed variables. Also, the method may include altering one or more variables of the simulated organic life model based on one or more variables of the simulated environment. Additionally, the method may include producing output data sets containing a continuum of data ranging from the data stream to predicted endpoint values for each data stream variable. Also, the method may include changing the simulated organic life model based on the altered one or more variables of the simulated organic life model.

BRIEF DESCRIPTION OF THE FIGURES

These and other features, aspects, and advantages of the present disclosure are better understood when the following Detailed Description is read with reference to the accompanying drawings.

FIG. 4a is a schematic of the example simulation;

FIG. 4b is a depiction of the processing of the example simulation;

FIG. 5e is a depiction of an example table indicating example results of FIGS. 5b-5d as compared to FIG. 5a.

FIG. 7a is a depiction of one example embodiment of a user interacting with a simulated environment;

FIG. 8a is a depiction of an example embodiment of an interactive virtual reality system;

DESCRIPTION OF EMBODIMENTS

Figure 1:
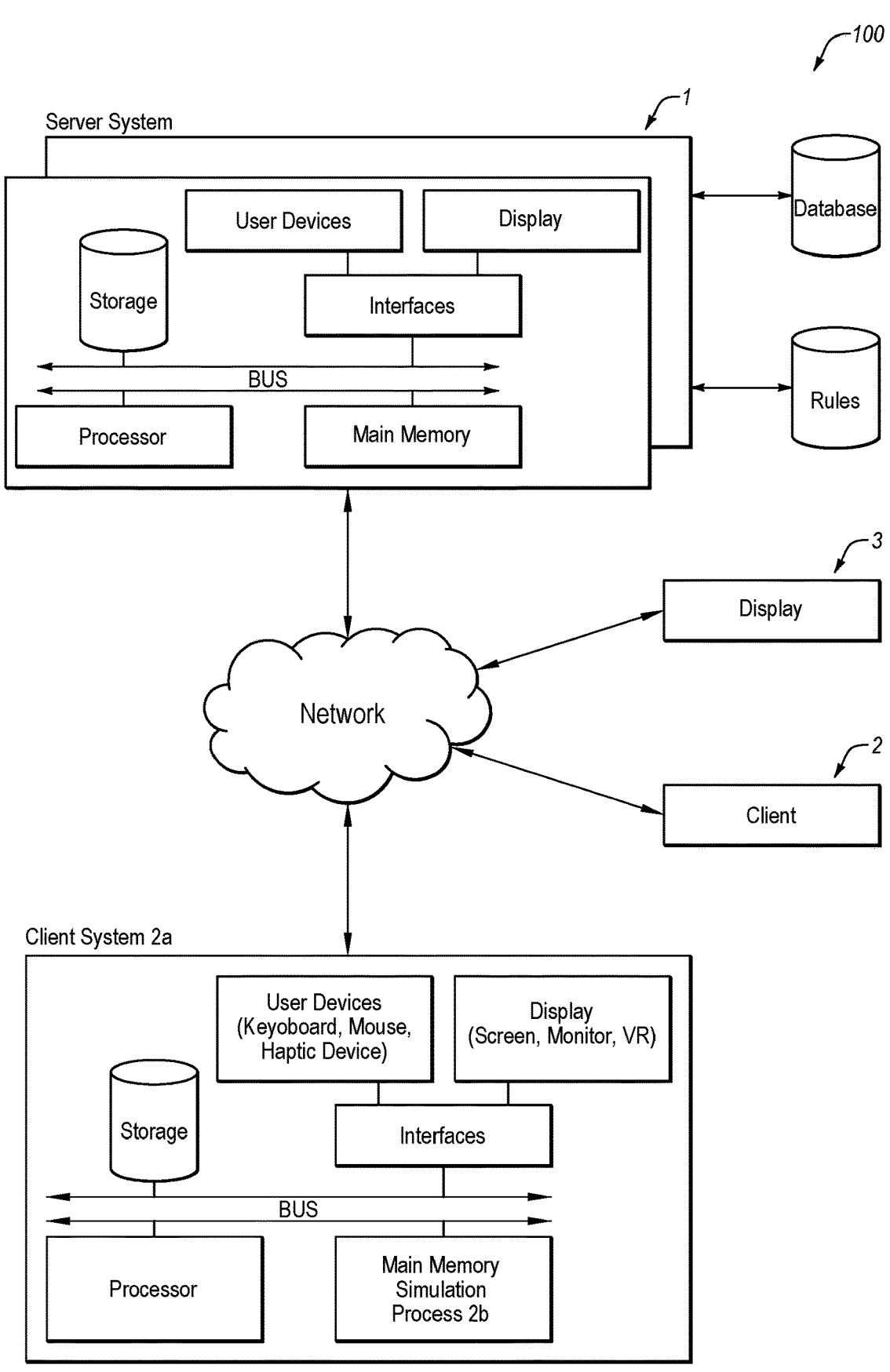
FIG. 1 is a depiction of an example system to simulate and display complex data.

Through a computer system that simulates and displays complex data as organic life models, users can monitor and compare non-text visual simulations providing a mechanism to predict data sets and compare outcomes without needing to see a text or numerical display. The computing system can be any sort of user client device or can be a server computing system that processes, simulates, generates, retrieves, and presents rendered simulations by a display (or virtual reality display system) associated with the client device (e.g., personal computer, tablet computer, smart phone) or can be a stand-alone display that receives the generated/retrieved simulations/animations/renderings via the client device and/or server.

Simulating highly complex data sets using organic life models provides an easily interpretable means to predict, forecast, and compare possible outcomes for the accumulated data sets, without being an expert in the area from which that data is derived.

Organic life in its essence is a characteristic distinguishing physical entities having signaling and self-sustaining processes from those that do not, either because such functions have ceased (death) or because they lack such functions and are classified as inanimate.

This organic life can be mathematically modeled and thus can be simulated. These simulated models may indicate and predict how this organism will fare within an also simulated environment.

Within simulated organic life models, intrinsic variables that make up the organisms' physical make up, behavior, signaling, and self-sustaining processes may describe and determine the model's ability to persist, grow, adapt, flourish, or die. The simulated environment in which the model responds provides extrinsic variables which may in turn affect the model organisms' own physical make up, behavior, signaling, and self-sustaining processes, inherent to its ability to persist, grow, adapt, change character, become damaged, flourish, or die. By proportionally parsing external data sets into the variables of the simulated organic life model's signaling and self-sustaining processes, as well of that of the simulated environment it resides in, the outcomes of the organic life model may be simulated and predicted with these new variables in place, altering the organic life model's ability to persist, grow, adapt, break or become damaged, flourish, or die, and simulating and predicting possible outcomes from the external data set or sets.

In some embodiments, in response to determining possible outcomes, a user or client, the client system, and/or the server system may perform some act in reality (e.g., outside the simulation). The act may be an affirmative act such as hiring a particular person, selling a specific stock, or optimizing file paths for reduced network congestion. The act may also be a passive act such as allowing a condition to subsist, maintaining the status quo, or continuing usual participation in a market trend. In some embodiments, the act may be an act of omission (e.g., choosing not to do something) such as choosing not to sell a stock, choosing not to join a union, or choosing not to reallocate storage at some server location. In each example of the affirmative act, the passive act, and/or the act of omission, the act performed in response to the determined possible outcome may correspond to at least one variable of the data stream parsed into one or both of the simulated organic life model and the simulated environment.

In these or other embodiments, one or more steps as illustrated in various figures herein and/or the affirmative act, the passive act, and/or the act of omission described above may improve the functioning of computers and network environments. For example, in response to processing the simulation of the simulated organic life model in the simulated environment based on the parsed variables, and in response to altering or stabilizing one or more variables of the simulated organic life model, possible future outcomes may be predicted and certain acts may be performed which may improve the functioning of any of the processor(s) and server(s) in the server system and/or client system may be improved. For example, any of these computer systems may be improved by optimization of various variables, which in turn may lead to any or all of the following: reduced computational overhead and network congestion, reduced down-time, better efficiency, lower error margins in analytic output, reduced sizing of required computational power in processors or servers, or increased speed of network functionality. Additionally, the methods herein described may iteratively improve various variables via mutations or stepwise variations based on the altering or stabilizing of variables of the simulated organic life model, for example, until a selectable threshold amount of improvement is met. The methods herein described may thus result in, for example, an optimized topology that is more effective and efficient than conventional topologies which may be directed to only classic problems (one-size-fits-all approach) and are not optimized for specific tasks. Thus, the methods described herein may be scalable for large-scale applications whereas inefficiencies of non-optimized variables may only percolate and/or grow into expansive network restrictions. Further, the resultant optimized variables using the methods described herein are superior to conventional methods where the optimization solution may not be readily transferrable to reality (e.g., outside of simulation) or the solution may not be readily apparent to persons without sufficient expertise or means of interpretation. For example, conventional methods may not understandably communicate which server host needs additional storage allocation to reduce the network congestion.

Also, methods described herein may improve the technical field of predictive/simulation analytics due to increased access to solutions and possible outcomes. For example, a greater number of individuals may be able to perform and understand possible outcomes and corresponding variables of focus to more likely achieve the possible outcome. Such methods described herein are an improvement over conventional methods which may be inefficient due to being incomprehensible to a great number of persons, which in some applications or examples may lead to an unnecessarily oversized topology with excess computational overhead, decreased performance (e.g., speed performance), or unnecessary/forced parameters limiting compatibility (e.g., for installation on embedded devices) or functionality for a given objective.

According to an aspect, a method includes receiving by one or more computers a data set, applying by the one or more computers the data set to a parsing rules engine to determine a particular value of the data set to be proportionally applied to an intrinsic variable of the simulated organic life model or models to be simulated. This may be repeated to some or each of the variables to be simulated within the organic life model or models. Additionally, the data set, may be applied to a parsing rules engine to determine a particular value or continuum of the data set to be proportionally applied to an extrinsic variable of the simulated environment of the organic life model or models. This may be repeated to some or each of the variables to be applied to the simulated environment of the organic life model. The simulation may be initiated and the interplay of extrinsic and intrinsic variables in each simulated organic life model, or models, revealed, causing the ability of the simulated organic life model or models to persist, grow, adapt, change character, flourish, become damaged, or die, and indicating to the user possible outcomes and/or comparisons between simulated organic life models, thus predicting possible outcomes in the external dataset.

According to an additional aspect, a method includes visualization of the simulation, including tabular data and/or models in 2D or 3D of the organic life model, within a simulated environment, indicating a real-time current status, a defined end point, or an animated sequence of time points if a continuum of data variables are applied.

According to an additional aspect, a computer program product tangibly stored on a computer readable storage device includes instructions for causing a processor to receive a live data stream or multiple live data streams, apply the data stream to a parsing rules engine to determine a value corresponding to a change between a current value of a specific variable in the data stream and the same variable at a previous time in the data stream, and use the determined change in the variable to alter a proportional intrinsic variable in the simulated organic life model or a proportional extrinsic variable in the simulated environment of the organic life model. The simulation may be processed and the interplay of extrinsic and intrinsic variables of some or each organic life model revealed, causing the ability of the simulated organic life model to persist, grow, adapt, change character, flourish, become damaged, or die. The simulation may be visualized in real time, as a stored section of the continuum or at a single defined point as tabular data, and/or models in 2d or 3D of the organic life model within its simulated environment as still images or an animated sequence of time points.

Additionally or alternatively, in some embodiments, changes in the model, whether changes to intrinsic or extrinsic variables, can either be observed directly by the user, or indicated and directed to the user through an artificial intelligence system trained to identify optimal qualities and outcomes of a given scenario and/or user preferences.

Computer driven displays and immersive virtual reality devices (head mounted or wall, floor, or ceiling mounted) produce depictions that enable users to passively or actively view and/or compare simulated organic life models, in process (live, real-time), after processing as an animation, as still images at specific time points during the simulation or as an end result of the simulation, in a non-text visual manner without the need to see and interpret numbers.

User driven pointing devices and interactive haptic response systems allow for virtual simulated interaction with organic life models within their simulated environment, translating object variables in the simulation into the corresponding sensations on the user's body, and vice versa, translating user movement, pressure, and manipulation into changes in the intrinsic simulated organic life model, or models, variables, and/or extrinsic environment variables within the simulation. This can in turn alter the ability of the simulated organic life model to persist, grow, adapt, change character, flourish, become damaged, or die within the simulated environment.

The details of one or more embodiments are set forth in the accompanying drawings and the description below. Other features, objects, and advantages of various embodiments may be apparent from the description and drawings, and from the claims.

These illustrative embodiments are mentioned not to limit or define the disclosure, but to provide examples to aid understanding thereof. Additional embodiments may be discussed herein. Advantages offered by one or more of the various embodiments may be further understood by examining this specification or by practicing one or more embodiments presented.

Referring now to FIG. 1, a system 100 to simulate, display, and/or visualize complex data may include a number of server systems 1, a number of client systems 2a, a network, and a display 3. Although illustrated as a single server system 1, in some embodiments the system 100 may include multiple server systems 1. In some embodiments, the server system 1 may include one or more processors, one or more storages, one or more main memories, one or more interfaces, one or more user devices, one or more displays, and/or one or more buses.

The server can be any of a variety of computing devices capable of receiving information, such as a server, a distributed computing system, a desktop computer, a laptop, a cell phone, a rack-mounted server, and so forth. The server may be a single server or a group of servers that are at a same location or at different locations.

The server can receive information from client devices via interfaces. The interfaces may be any type of interface capable of receiving information over a network, such as an Ethernet interface, a wireless networking interface, a fiber-optic networking interface, a modem, and so forth. The server may also include a processor and memory. A bus system (not shown), including, for example, an information bus and a motherboard, may be used to establish and to control information communication between the components of the server.

The processor may include one or more microprocessors. Generally, the processor may include any appropriate processor and/or logic configured for receiving and storing information, and for communicating over a network (not shown). Memory can include a hard drive and a random access memory storage device, such as a dynamic random access memory, machine-readable media, or other types of non-transitory machine-readable storage devices.

The components may also include a storage device, which may be configured to store information, map, map templates, rules information for the rules, software for the rules engine, etc.

Embodiments can be implemented in digital electronic circuitry, in computer hardware, firmware, software, or in combinations thereof. An apparatus can be implemented in a computer program product tangibly embodied or stored in a machine-readable storage device and/or machine readable media for execution by a programmable processor; and method actions can be performed by a programmable processor executing a program of instructions to perform functions and operations by operating on input information and generating output. Aspects can be implemented advantageously in one or more computer programs that are executable on a programmable system including at least one programmable processor coupled to receive information and instructions from, and to transmit information and instructions to, an information storage system, at least one input device, and at least one output device. Some or each computer program may be implemented in a high-level procedural or object oriented programming language, or in assembly or machine language if desired; and in any case, the language may be a compiled or interpreted language.

Suitable processors include, by way of example, both general and special purpose microprocessors. Generally, a processor may receive instructions and information from a read-only memory and/or a random access memory. Generally, a computer may include one or more mass storage devices for storing information files; such devices include magnetic disks, such as internal hard disks and removable disks; magneto-optical disks; and optical disks as well as solid state disk drives. Storage devices suitable for tangibly embodying computer program instructions and information include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

The various flowcharts, processes, computers, servers, etc., described in this document may be executed, for example, using the server system 1 (or processing unit) illustrated in FIG. 1. For example, the server system 1 can be used alone or in conjunction with other components. As another example, the server system 1 can be used to perform any calculation, solve any equation, perform any identification, and/or make any determination described here.

The server system 1 may include any or all of the hardware elements shown in the figure and described herein. The server system 1 may include hardware elements that can be electrically coupled via a bus (or may otherwise be in communication, as appropriate). The hardware elements can include one or more processors, including, without limitation, one or more general-purpose processors and/or one or more special-purpose processors (such as digital signal processing chips, graphics acceleration chips, and/or the like); one or more input user devices, which can include, without limitation, a mouse, a keyboard, and/or the like; and one or more output devices, which can include, without limitation, a display device, a printer, and/or the like. In some embodiments, the server system 1 may include a dedicated embedded processor chip such as, for example, a processor on a motherboard of a graphics processing unit (GPU).

The server system 1 may further include (and/or be in communication with) one or more storage devices, which can include, without limitation, local and/or network-accessible storage and/or can include, without limitation, a disk drive, a drive array, an optical storage device, a solid-state storage device, such as random access memory ("RAM") and/or read-only memory ("ROM"), which can be programmable, flash-updateable, and/or the like. The server system 1 may also include a communications subsystem, which can include, without limitation, a modem, a network card (wireless or wired), an infrared communication device, a wireless communication device and/or chipset (such as a Bluetooth® device, a 802.6 device, a WiFi device, a WiMAX device, cellular communication facilities, etc.), and/or the like. The communications subsystem may permit data to be exchanged with a network (such as the network described below, to name one example) and/or any other devices described herein. In some embodiments, the server system 1 may further include a working memory, which can include a RAM or ROM device, as described above.

The server system 1 also may include software elements, shown as being currently located within the working memory, including an operating system and/or other code, such as one or more application programs, which may include computer programs of various embodiments and/or may be designed to implement methods of various embodiments and/or configure systems of various embodiments, as described herein. For example, one or more procedures described with respect to the method(s) discussed above might be implemented as code and/or instructions executable by a computer (and/or a processor within a computer). A set of these instructions and/or codes may be stored on a computer-readable storage medium, such as the storage device(s) described above.

In some cases, the storage medium may be incorporated within the server system 1 or in communication with the server system 1. In other embodiments, the storage medium might be separate from the server system 1 (e.g., a removable medium, such as a compact disc, etc.), and/or provided in an installation package, such that the storage medium can be used to program a general-purpose computer with the instructions/code stored thereon. These instructions might take the form of executable code, which is executable by the server system 1 and/or might take the form of source and/or installable code, which, upon compilation and/or installation on the server system 1 (e.g., using any of a variety of generally available compilers, installation programs, compression/decompression utilities, etc.), then takes the form of executable code.

In some embodiments, the system 100 may include a client system 2a. Although illustrated as a single client system 2a, in some embodiments the system 100 may include multiple client systems 2a. In some embodiments, the client system 2a may include one or more processors, one or more storages, one or more main memories, one or more interfaces, one or more user devices, one or more displays, and/or one or more buses. In some embodiments, the user devices may include keyboards, mice, haptic devices, microphones, and/or any other user device that may be capable of providing an input signal to the client system 2a. In some embodiments, the display may include a screen, a monitor, a television, a VR headset, a display on a handheld device, and/or any other display that may be capable of providing a visual display to a user. In some embodiments, the memory and/or the main memory may store a computer program product that provides a simulated organic life model simulation process 2b (as illustrated in the main memory of client system 2a).

In some embodiments, the system 100 may include a network. The network may include a wide area network such as the Internet, a local area network, and/or any other network that may be configured to connect the server system 1, the client system 2a, and/or other devices.

In some embodiments, the server system 1 may produce data streams for client system 2a from real-time data information that is sent to the server system 1. When executed, the computer program product may configure the server system 1 to send the data streams from the server system 1 to one or more clients 2 or displays 3. The data streams may include data that renders graphical, non-numeric depictions of simulated organic life models. In other embodiments, the client system 2a may execute the simulation process 2b, as illustrated. The client system 2a may receive the real-time simulation data information directly and produce the simulated organic life models within a simulated environment. In these and other embodiments, the computer program product may configure the client system 2a to send the data streams from client system 2a to one or more clients 2 or displays 3.

In some embodiments, the data can be delayed, e.g., from seconds to weeks. This may be because generally distributors of data may charge fees for the data, with the fees possibly tied to the age of the data. Real-time data, e.g., milliseconds or seconds old, may command pricing that would not be practical for all users. Thus, in some instances real-time data may not be used, but instead the data would be delayed. Both real-time and delayed data are within the scope of the embodiments discussed herein.

In some embodiments, the client system 2a and/or the server system 1 of the system 100 may access a database that may store historical information and/or user preferences, pre-calculated simulations, models, and graphics. In some embodiments, a parsing rules engine that may execute on the server system 1 and/or the client system 2a may retrieve the user preferences and may receive the real-data as well as retrieve historical data information, pre-calculated simulations and organic life models e.g., from the database or a similar source to execute the simulation process 2b.

Figure 2:
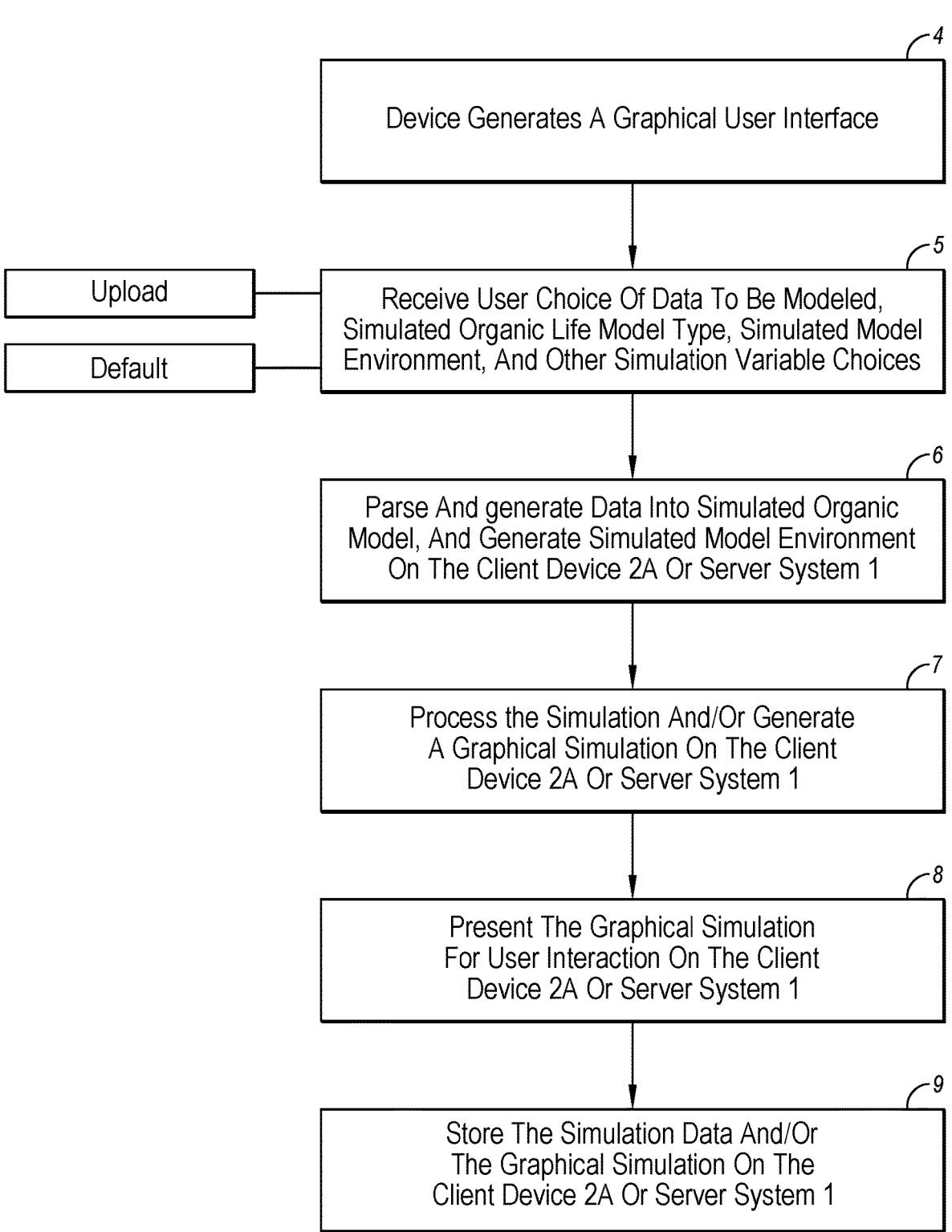
FIG. 2 is a depiction of an example simulation process.

Referring now to FIG. 2, the simulation process 2b is depicted. In some embodiments, in box 4 the simulation process may generate a graphical user interface. The graphical user interface may be displayed on a display such as the display of the client system 2a or the display 3 of FIG. 1. The graphical user interface may present a user with options to select the data to be modeled, the type of simulated organic life model to be used, the type of simulated environment the organic life model may be simulated in, and variables that may alter the stringency of the simulation.

In some embodiments, the simulated organic life models may be of various types including plants, animals, and other organic life. The simulated organic life models may derive their ability to persist, grow, adapt, change character, flourish, become damaged, or die from parsed data variables applied to them. In response to the variables and the simulated environment, the appearance of the simulated organic life models may change, as will be discussed below. In some embodiments the graphical visualization of the simulation for the one or more data sets may be animated in appearance, changing their appearance based on the intrinsic variables of the simulated organic life model and extrinsic variables of the simulated environment in which they reside. These visual simulations may vary in appearance according to the status of the input data set, live data feed, and/or historical data as applied to the intrinsic variables of the simulated organic life models or to the extrinsic variables of the simulated environment. In some embodiments, the appearance may change in a continuum, according to their ability to persist, grow, adapt, change character, flourish, become damaged, or die.

Additionally or alternatively, in some embodiments, changes in the model, whether changes to intrinsic or extrinsic variables, can either be observed directly by the user, or indicated and directed to the user through an artificial intelligence system trained to identify optimal qualities and outcomes of a given scenario and/or user preferences.

In some embodiments, in box 5, the simulation process 2b may receive the user selections for some or each of the options presented to the user in box 4. In some embodiments, the user may perform the selection through, e.g., the user devices of client system 2a. For example, in some embodiments, the user may select options by use of a keyboard or a mouse configured to provide input to the client system 2a. Alternatively or additionally, in some embodiments, the user may select options by use of a haptic device. Alternatively or additionally, the selections of the data to be modeled, simulated organic life model type, simulated model environment, and other simulation variable choices may be made through an uploaded selection and/or a default selection. The default selection may select values for some or each of the choices that may correspond with the most frequently chosen options of the user or the most frequently chosen options of some or all users. In some embodiments, the user provided selection of data to be modeled, simulated organic life model type, simulated model environment, and other variable choices, may be either stored on the server system 1 or the client system 2a.

In some embodiments, a user may set "weather" scenarios which may mimic extrinsic variable changes such as market conditions. Alternatively or additionally, in some embodiments the simulation process may model the spread of a negative effects in market conditions, which may be similar to modeling a blight or disease as it spreads through a population of plants and/or the market sector.

In some embodiments, in box 6, the selected data may be parsed and generated into the simulated organic model and the simulated model environment may be generated on the client system 2a and/or the server system 1. In some embodiments, the parsing of the data may include matching current and/or historical data variables with intrinsic variables describing the simulated organic model. For example, when the simulated organic model is a plant or a tree, the intrinsic variables of the corresponding simulated organic life model may include but not be limited to such things as age, height, trunk thickness, growth rate, root growth rate, canopy size, leaf size, fruit types and size, hardiness, shoot growth, branching geometry, competition from neighboring trees on the structural dynamics of the tree crown, the distribution of carbohydrates between productive and non-productive tissues, light interception properties and local light climate, gas-exchange properties, interception of light by leaves and bending of branches due to gravity, branching habits, radiation absorption and carbon gain, and root growth and architecture.

In some embodiments, the extrinsic variables may be dependent on the type of simulation that is performed. For example, for a land-based simulation, extrinsic variables may include, but are not limited to: gravity; location, including longitude, latitude, and elevation, which may affect temperature, light intensity, light duration, and radiation intensity; air particulates; weather including wind strength, direction, turbulence, and duration, humidity, air pressure, light intensity, and precipitation duration, rate, size, and type including rain, hail, and snow; soil environment including nutrient content, water content, drainage (granularity), and pH; pests including vermin, birds, insects, and infectious agents; and disasters including earthquakes, landslides, floods, tsunamis, volcanos, magma flow, hurricanes, fires, asteroid impacts, and war. In some embodiments, additional extrinsic variables may be used for a land-based simulation.

In some embodiments, for a water-based simulation, extrinsic variables may include, but are not limited to: gravity; location, including longitude, latitude, depth, and elevation; temperature; light intensity; radiation levels; light duration; weather above the water including wind strength, direction, turbulence, and duration, humidity, air pressure, light intensity, and precipitation; liquid environment including nutrient content, pH, water pressure, salinity, and current strength, direction, turbulence, and duration; and disasters including earthquakes, landslides, floods, tsunamis, volcanos, magma flow, hurricanes, fires, asteroid impacts, and war. In some embodiments, additional extrinsic variables may be used for a water-based simulation.

In some embodiments, for an air-based simulation, extrinsic variables may include, but are not limited to: gravity; location, including longitude, latitude, and altitude; weather including wind strength, direction, turbulence, and duration, humidity, air pressure, light intensity, and precipitation; and disasters including earthquakes, landslides, floods, tsunamis, volcanos, magma flow, hurricanes, fires, asteroid impacts, and war. In some embodiments, additional extrinsic variables may be used for an air-based simulation.

In some embodiments, for a simulated organic life model for a tree, intrinsic variables may include, but are not limited to: the trunk including height, diameter, age, fiber density, strength including torsion, elasticity, and flexibility, and density; the branches including number, thickness, flexibility, number of sub-branches, and number of leaves; the leaves including area (wind shear), size (large leaves lots of photosynthesis), and color; the roots including number, thickness, flexibility, number of sub-roots, branching, depth, and strength; the growth rate; and the tree type. In some embodiments, additional intrinsic variables may be used for a simulated organic life model for a tree. In these and other embodiments, comparable intrinsic variables for a simulated organic life model for an animal could be identified such as, for example, bone strength, metabolism, breeding rate, social structure, muscle density, speed, lifespan, and size.

In some embodiments, the extrinsic and intrinsic variables of the simulated organic life model may be parsed from a complex data set such that one or more other complex data sets such as economic markets, security systems, employment systems, national systems, weapons systems, health management systems, among others, may be simulated using the organic system as a representation of the complex data set.

For example, in some embodiments, the extrinsic and intrinsic variables may be parsed into economic performance indicators. For example, extrinsic and intrinsic variables of organic models may be parsed into intrinsic economic performance indicators of a system. For example, extrinsic and intrinsic variables of a tree may be parsed into the intrinsic economic performance indicators of a system. Intrinsic economic performance indicators may include, but are not limited to: overall performance of the economy including average annual gross domestic product (GDP), GDP per capita, human development index (HDI), multidimensional poverty index, gender inequality index, seats in parliament held by women (as a percent of total), and composite risk rating; the economic regime including gross capital formation as a percent of GDP (average), trade as a percentage of GDP (may also be an extrinsic variable), tariff and nontariff barriers (may also be an extrinsic variable), soundness of banks, exports of goods and services as a percentage of GDP (may also be an extrinsic variable), interest rate spread (lending rate minus deposit rate) (may also be an extrinsic variable), intensity of local competition, domestic credit to private sector (percentage of GDP), cost to register a business (percentage of gross national income per capita), days required to start a business, and cost to enforce a contract (percentage of debt); governance including regulatory quality, rule of law, government effectiveness, voice and accountability, political stability, control of corruption, and press freedom; the innovation system including foreign direct investment (FDI) outflows as a percentage of GDP (may also be an extrinsic variable), FDI inflows as a percentage of GDP (may also be an extrinsic variable), royalty and license fees payments, royalty and license fees payments per million population, royalty and license fees receipts, royalty and license fees receipts per million population, royalty and license fees payments and receipts, royalty and license fees payments and receipts per million population, science and engineering enrollment, science enrollment ratio, researchers in research and development (R&D), researchers in R&D per million population, total expenditure for R&D as a percentage of GDP, manufacturing trade as a percentage of GDP (may also be an extrinsic variable), university-company research collaboration, scientific and technical journal articles, scientific and technical journal articles per million population, availability of venture capital, patent applications granted by the USPTO, patent applications granted by the USPTO per million people, high-technology exports as a percentage of manufactured exports (may also be an extrinsic variable), private sector spending on R&D, firm-level technology absorption, value chain breadth, capital goods gross imports (as a percentage of GDP) (may also be an extrinsic variable), capital goods gross exports (as a percentage of GDP) (may also be an extrinsic variable), science and engineering articles with foreign co-authorship (percentage), average number of citations per science and engineering article, and intellectual property protection; education including adult literacy rate (percentage age 15 and above), average years of schooling, secondary enrollment (percentage of gross), tertiary enrollment (percentage of gross), life expectancy at birth (may also be an extrinsic variable), Internet access at schools, public spending on education as a percentage of GDP, 4th grade achievement in mathematics, 4th grade achievement in science, 8th grade achievement in mathematics, 8th grade achievement in science, quality of science and math education, quality of management education, 15-year-olds' math literacy, 15-year-olds' science literacy, school enrollment, no schooling, secondary school completion, and tertiary school completion; labor including unemployment rate (percentage of total labor force), unemployment rate, employment in industry (percentage of total employment), employment in services (percentage of total employment), professional and technical workers as a percentage of the labor force, extent of staff training, brain drain, cooperation in labor-employer relations, flexibility of wage determination, pay and productivity, reliance on professional management, local availability of specialized research and training services, difficulty of hiring index, rigidity of hours index, difficulty of redundancy index, redundancy costs, labor tax and contributions (percentage), employment to population ratio, unemployment with tertiary education, unemployment with secondary education, labor force participation rate, youth unemployment rate, adult unemployment rate, share of youth unemployment in total unemployment, long-term unemployment, labor force with tertiary education (percentage of total), labor force with secondary education (percentage of total), firms offering formal training (percentage of firms), and females in labor force (percentage of total labor force); and information and communication technology including telephones per 1000, telephone mainlines per 1000, mobile phones per 1000, computers per 1000, TV households with television, daily newspapers per 1000, international Internet bandwidth (bits per person) (may also be an extrinsic variable), Internet users per 1000, fixed broadband Internet access tariff (United States dollars per month), availability of e-government services, government online service index, and ICT expenditure as a percentage of GDP. In some embodiments, additional variables may be used for simulation. In these and other embodiments, comparable variables for a simulated organic life model for a company could be identified such as, for example, dividend payout ratio, historical dividend growth, gross margin, and revenue growth rate.

In some embodiments, the complex data set may include data related to personnel or potential personnel at a company. For example, the data may include the number of jobs held by an individual, the length of employment, the intellectual requirement for a job opening, IQ, and EQ, among other variables related to an individual.

In some embodiments, the variable parsing engine may parse the external variables to extrinsic and intrinsic variables of a security information and event management system, which may include variables related to server security, server load, internet statistics, web statistics, cyber-attack situations, and/or other situations. In these and other embodiments, a cyber-attack may include an offensive attack that targets computer networks, personal computing devices including smartphones, tablets, desktop computers, and laptop computers, computer infrastructures, and/or computer information systems to steal, alter, destroy, and/or corrupt items in the targeted system. Additionally or alternatively, the complex data may pertain to network breaches, firewalls, health, server functionality, and/or other information. In these and other embodiments, a graphical depiction of a security information and event management system may allow a user to rapidly interpret complex data and make a logistical decision. In these and other embodiments, it may be difficult to understand the complex data set in a numeric, tabular, and/or chart form.

In some embodiments, the external variables may include variables related to real-time national systems, combat and weapon systems and sensors, and other tactical data sources. In these and other embodiments, simulation of real-time national systems, combat and weapon systems and sensors, and other tactical data sources may enable and enhance threat assessment and prediction, combat ID, integrated fires, and mission planning and execution. In some embodiments, simulation may facilitate information processing, prediction, and visualization to support tactical war fighting. In these and other embodiments, a graphical depiction of real-time national systems, combat and weapon systems and sensors, and other tactical data sources may allow a user to rapidly interpret de-convolved data from disparate sensor types, in a clear and immediately interpretable visualization, and make a logistical decision without expertise in the field. In these and other embodiments, prediction, simulation and visualization of filter thresholds and clustered snippets may improve recognition while controlling a false alarm rate. In some embodiments, simulation of variables may facilitate monitoring, predicting, and visualizing differences between expected conditions and encountered conditions in in-situ acoustic data or oceanographic data.

In some embodiments, the external variables may include variables related to prediction, simulation, and visualization of Blue (own or allied) operational behaviors, characteristics, and performance. In these and other embodiments, Blue may be used to signify one's own forces, as opposed to Red, which may signify enemy forces, and White, which may signify neutral forces. In these and other embodiments, simulation and visualization may facilitate spawning recalculation prediction and re-visualization. In some embodiments, the external variables may include variables related to prediction, simulation, and visualization of threat probability density, including, for example data from track association, Identification Friend-or-Foe (IFF)/Automatic Identification System (AIS) data, flight plans, schedules, air routes, intelligence information, collected second and third tier information sources in addition to primary sources, for example shipping lanes and fishing areas. In these and other embodiments, simulation and visualization may improve identity classification, intent and future movement prediction. In these and other embodiments, organic sensor information may be used to recommend the identification of a track, to predict the intent and future movement of a track, and/or recommend the association of the track with another track.

In some embodiments, the external variables may include variables related to prediction, simulation and visualization of unexpected Red (enemy) Air and Missile capabilities, behaviors, and operational patterns. In some embodiments, the external variables may include variables related to intelligence information, missile models, historical measurements, intelligence threat library (e.g. anti-ship cruise missile/ballistic missile radar, electronic warfare, and infrared signatures) data sets, live sensor data, and electronic warfare/non-cooperative target recognition data. In these and other embodiments, simulation and visualization may be used to identify new capabilities, behaviors, and operational patterns and may possibly recommend new system settings to address them. In some embodiments, simulation and visualization may be used to improve planning of asset movement and tactical utilization, optimize weapon usage, improve spectrum operations, and improve situational awareness. In these and other embodiments, simulation and visualization may use current, predicted, and historical movements of Red (enemy)/White (neutral)/Blue (own)

assets and intelligence sources to identify information that may trigger a warfighter notification. In these and other embodiments, prediction, simulation and visualization of tactical data may help validate or estimate the trustworthiness of the data and may help determine the likelihood that a piece of data has been tampered with.

In some embodiments, the variable parsing engine may parse the external variables of health management systems to extrinsic and intrinsic variables of a simulated organic life model. For example, the parsing of the variables and the simulation of the variables of health management systems may enable prediction, simulation and visualization of risk analysis; enable lifestyle management and monitoring; facilitate imaging and diagnostics; further drug discovery; simplify emergency room and hospital management; facilitate operation of mental health departments; help with virtual assistant integration; and facilitate research analysis. By parsing the external variables of health management systems to a simulated organic life model, facets of the health management systems may be more readily observed by those not necessarily expert in the field. Additionally, in some embodiments, a graphical presentation of the simulated organic life models may allow the rapid comparison of the complex data set, such as the health management system, represented by the simulated organic life model. In these and other embodiments, some or each simulated organic life model may represent many health management system variables for a company. When presented in a tabular form, it may be difficult for a non-expert user to understand and/or interpret the data. By presenting the data as a simulated organic life model, a non-expert user may be able to better understand, interpret, and/or use the data to make a decision. The parsing of the external variables of health management systems may enable individuals to comprehend, compare, and decide on important aspects of health management administration, patient health decisions, and cost management determination.

In some embodiments, the variable parsing engine may parse the external variables of individuals to extrinsic and intrinsic variables of the tree. For example, the parsing of the variables and the simulation of the variables may be used in some embodiments to rank personnel, for interview triage, and/or for hiring the best person for the job. In these and other embodiments, the simulation and/or the variable parsing may help identify which person overall is best for a job. In these and other embodiments, the tree with the most fruit may indicate the potential employee who may be most effective in the workforce. In these and other embodiments, the tree that is strongest in the wind may indicate the potential employee who may be most resilient.

In some embodiments, users may select various simulated organic life models to represent their choice of data to be simulated or data of interest to the user. In some embodiments, users can view and interact with graphical simulations 8, identifying and interpreting the simulation in relevance to the input data sets. For example, marketing campaigns or economic and financial data could be simulated in this system. In these and other embodiments, tree or plant simulations may represent complex Internet marketing campaign data, whole countries' economic data, or companies traded in a stock market.

In some embodiments, in box 7, the simulation may be processed and a graphical depiction of the simulation may be generated on the client system 2a and/or the server system 1. In some embodiments, in order to predict the effect of economic or financial scenarios on a marketing campaign, on countries' economic outcomes, or on a collection of companies in a stock market, simulated extrinsic variables of the simulated environment may be altered and applied to the simulated organic life models within, which may alter the ability of the models to persist, grow, adapt, change character, flourish, become damaged, or die. For example, if a user wished to predict the effect of reduced worldwide market optimism, share price slumps, or federal interest rate increases on the financial "health" of countries worldwide or companies in a stock market, then actual, historical, or invented changes in these financial variables may be parsed into the simulated extrinsic variables of the simulated environment. In some embodiments, simulated environmental variables such as soil moisture, soil and air temperature, soil aeration, wind, rain, humidity, gravity, and sunlight could receive these parsed financial variables and in turn negatively affect the simulated organic life models, causing deterioration in their ability to persist, grow, adapt, or flourish, become damaged, and perhaps die. In some embodiments, drastically reducing the amount of simulated rain to a set of simulated organic tree models may cause some or all of them to deteriorate, lose leaves, wilt, and/or grow more slowly; those with "weaker" intrinsic variables may deteriorate faster and may perhaps die in the simulation. In some embodiments, other indicators may include less fruit, leaf deterioration, color change and loss, wilting, susceptibility to wind damage, branch, limb and trunk damage, uprooting by wind, and death by cold weather. In some embodiments, indicators of non-simulated variables may also be included. In these and other embodiments, when the simulated organic life model represents a company, the other indicators of non-simulated variables may include: tree bracing (which may indicate that the company has had a bail out); decorative tree lights and/or a tree topper with a variable brightness and number (which may be proportional to the number of mentions a company receives on social media); decorative ropes (shimenawa) with paper streamers (shide) which in Japanese culture may be used to venerate a tree (which may be added to a simulation to indicate a prestigious award received or milestone achieved by a company); a lumberjack or axe-man (which may indicate that the simulated company is in the process of being acquired by or merged with another company); and/or birds and other animals interacting with the tree, especially if there is fruit on the tree (which many indicate that the company is currently experiencing a high volume of trades).

In other embodiments, simulations may include other elements such as clouds, rain, rivers, waves, beaches, coral, sediment, and other natural elements and surroundings. In some embodiments, the proportional occurrence of these other elements may be determined by current or historical financial market conditions.

In these and other embodiments, the simulations may be performed using animal simulators, plant simulators, and/or other simulators which may include whole-organism simulators that may be based on detailed scientific knowledge of the organic life-form. For example, tree simulators may be based on botanical data and knowledge about factors, variables, and relationships related to the growth of a tree. As an additional example, animal simulators may be based on animal data, including data specific to a particular species, and knowledge about factors, variables, and relationships related to the growth of the particular species of animal.

In some embodiments, in box 8, the simulation may be presented graphically on the client system 2*a* and/or the server system 1. In addition, in some embodiments, a user may interact with the simulation. Continuing the example above, in some embodiments, the user may observe the visual changes such as less fruit, leaf deterioration, color change and loss, wilting, susceptibility to wind damage, branch, limb, and trunk damage, uprooting by wind, and death by cold weather in the graphical depiction of the simulation. In some embodiments, by comparing between models in the same simulation, a user may identify those simulated plants that fare better than others, indicating without use of text and numerical information that certain marketing strategies, countries, or companies may be a better or worse investment for the user in future suppressed financial scenarios.

In some embodiments, because the simulation takes into account more variables than can be seen by the user in isolation, the effects of the variables can be seen in a simulated organic life model whereas they could be missed through conventional analysis or observed but not taken into account.

Additionally or alternatively, in some embodiments, changes in the model, whether changes to intrinsic or extrinsic variables, can either be observed directly by the user, or indicated and directed to the user through an artificial intelligence system trained to identify optimal qualities and outcomes of a given scenario and/or user preferences.

In some embodiments, the original data set may be visualized together with the simulation. In these and other embodiments, the presentation of the original data and/or the simulation data in an organic life model simulation may allow a user to better understand the overall health of the object represented by the simulated organic life model. In some situations, a national economy and/or a company may have many financial metrics that may be difficult for a user to understand in isolation. By presenting the data in a simulated organic life model, the complex data may be visualized in a manner that is easier for a user to understand, manipulate, and/or process.

In some embodiments, in box 9, the user-provided selection and associations may be stored on the client system 2*a* and/or the server system 1. In these and other embodiments, the steps outlined above may be performed in a different order. Additionally or alternatively, one or more steps may be combined into fewer steps or divided into more steps.

Figure 3:
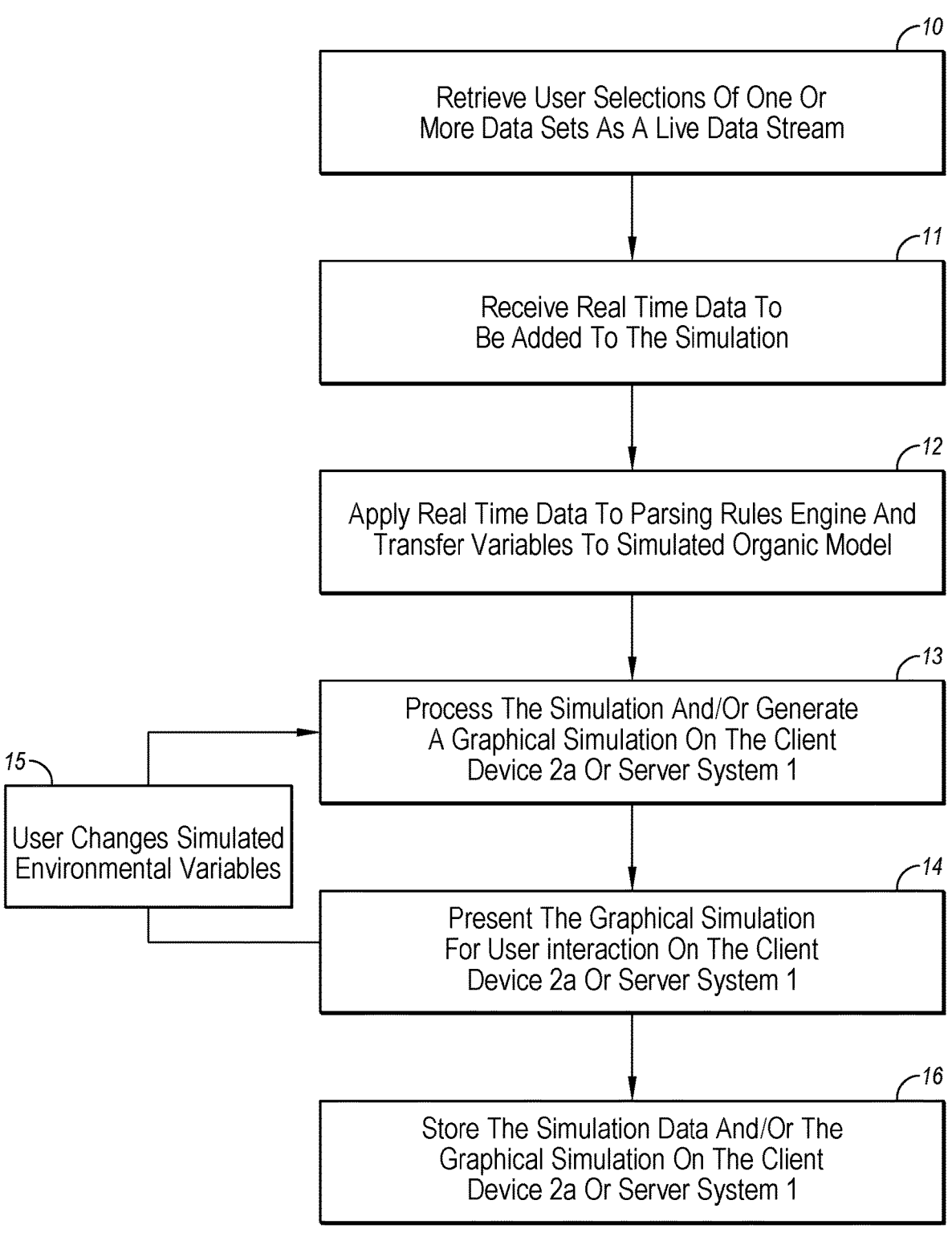
FIG. 3 is a depiction of an example simulation process using real-time data.

Referring now to FIG. 3, a simulation process using real-time data is depicted. In some embodiments, the simulation process depicted in FIG. 3 may be used to simulate financial markets and may obtain real-time and/or near real-time data from financial markets such as trading volume, trading price, bid-ask spread, and/or other data.

In some embodiments, in box 10 a simulation process, for example the simulation process 2*b* of FIG. 1, may retrieve user selections of one or more data sets and simulation types of interest to the user, once the user preferences are initiated. In some embodiments, the one or more data sets may be financial market data sets.

In some embodiments, in box 11, the simulation process may periodically, e.g., at regular intervals or continuously, receive real-time and/or near real-time data. In some embodiments, the real-time and/or near real-time data may include data of current market conditions including information such as market trading prices and/or volume for a selected business data set as well as general market trends and environment.

In some embodiments, in box 12, the simulation process may apply the real-time data stream to a parsing rules engine to determine proportional values to be applied to the intrinsic variables of the simulated organic life models, as well as general market environment variables to be applied to the extrinsic variables of the simulated environment. In some embodiments, the parsing rules engine may perform in a manner similar to the parsing and generating in box 6 of FIG. 2. In some embodiments, in response to determining some or all current variables, the simulation process may proceed to box 13.

In some embodiments, in box 13, the simulation process may process the simulation and/or generate a graphical simulation on the client system 2a and/or the server system 1. In some embodiments, the graphical simulation may be a depiction of the simulation process and/or the processed simulation.

In some embodiments, in box 14, the graphical simulation may be presented for user observation, interpretation, and/or interaction on a client system 2a and/or the server system 1.

In response to a change in an environmental variable, the simulation process may proceed to box 13 to process the simulation with the changed environmental variable. In some embodiments, the change in an environmental variable may be instantiated by a user. In some embodiments, the user may have the option to change the simulated environmental variables to a suggested set of preset variables offered to the user, simulating in general terms negative or positive market trends/environments, to a sliding set of values chosen by the user, and/or to other variable selections. In some embodiments, these changes in simulated environmental variables may affect the simulated organic life model's ability to persist, grow, adapt, or flourish, become damaged, and perhaps die; and may be predictive in indicating possible future outcomes, e.g., market trading prices and/or volume for selected businesses under extrinsic influences of global market trends and changes.

Additionally or alternatively, in some embodiments, changes in the model, whether changes to intrinsic or extrinsic variables, can either be observed directly by the user, or indicated and directed to the user through an artificial intelligence system trained to identify optimal qualities and outcomes of a given scenario and/or user preferences.

In some embodiments, in box 16, the simulation data and/or the graphical simulation may be stored for later analysis on the client system 2a and/or the server system 1.

In other embodiments, intrinsic organic model variables and extrinsic simulation environmental variables can be altered in real-time within the simulation through use of user devices, sensors, or probes, changing the simulated organic life models, and the simulated environment thus altering the simulated organic life models' ability to persist, grow, adapt, change character, flourish, become damaged, or die within the simulated environment.

Figure 4B:
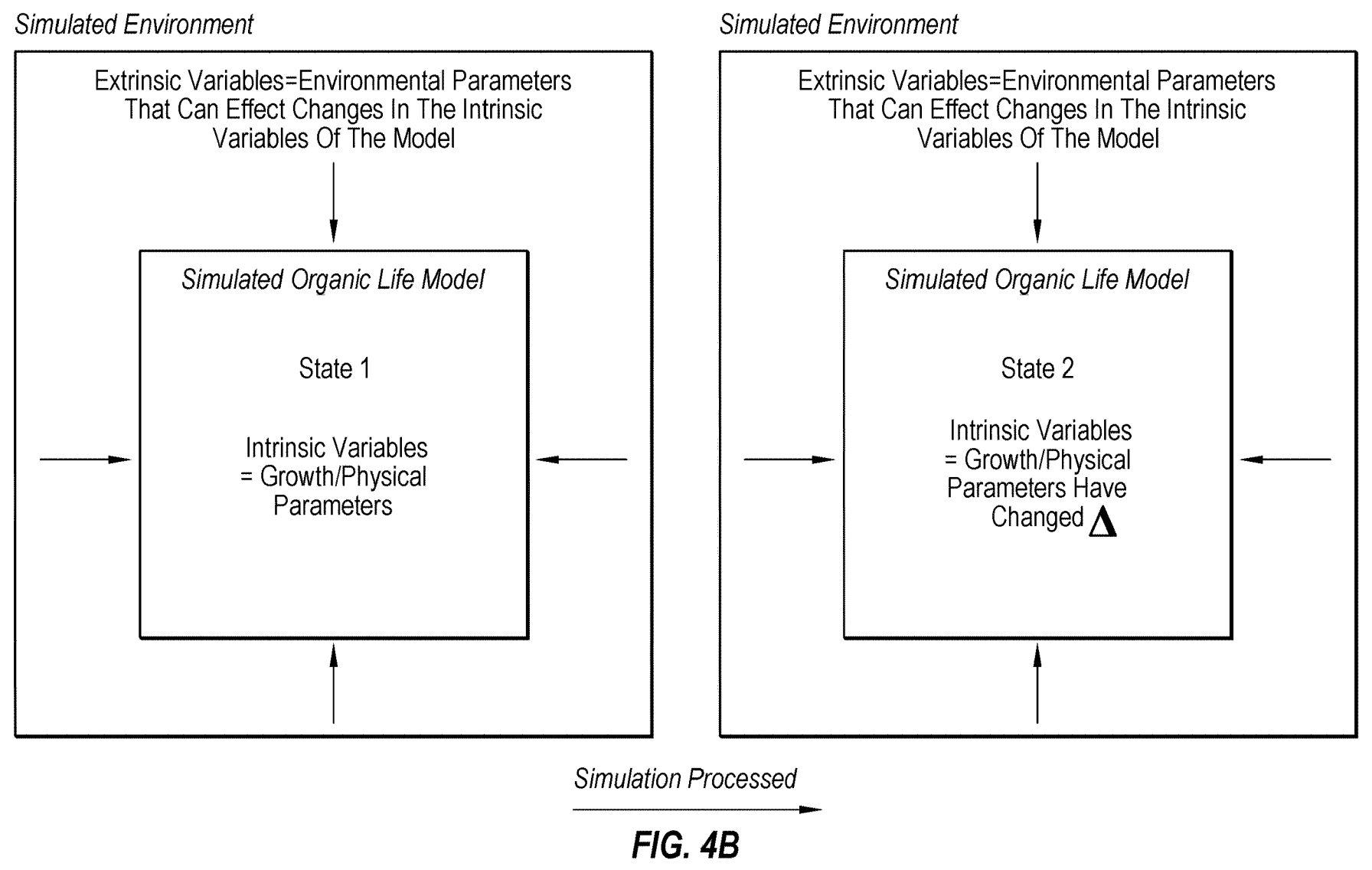

Referring now to FIGS. 4a and 4b, a schematic of the simulation is depicted. In some embodiments, the simulation may include a simulated environment and a simulated organic life model. In some embodiments, the simulated environment may include extrinsic variables, which may include environmental parameters that may effect changes in intrinsic variables of the simulated organic life model. The extrinsic variables may include parsed data or forecast scenarios describing the model effecting data. In some embodiments, the extrinsic variables may be parsed with the forecast scenarios or parsed data in, for example, box 6 of FIG. 2 and/or box 12 of FIG. 3.

In some embodiments, the simulated organic life model may include intrinsic variables, which may include growth or physical parameters. These parameters may be related to the ability and means of the model to persist, grow, change character, flourish, and/or die. The intrinsic variables may include parsed data describing the intrinsic variables of the model. In some embodiments, the intrinsic variables may be parsed with the parsed data in, for example, box 6 of FIG. 2 and/or box 12 of FIG. 3.

In FIG. 4b, the processing of the simulation is depicted. In some embodiments, as the simulation changes from State 1 to State 2, intrinsic variables of the simulated organic life model may change. In some embodiments, this may be depicted graphically as changes in the external appearance or health of the simulated organic life model. For example, in some embodiments the simulated organic life model may have undergone a negative change between State 1 and State 2. As a result, the simulated organic life model may be smaller, be less healthy, and/or have died. Alternatively or additionally, in some embodiments, the simulated organic life model may have undergone a positive change between State 1 and State 2. As a result, the simulated organic life model may be larger, healthier, and/or more robust in State 2 than it was in State 1.

Additionally or alternatively, in some embodiments, changes in the model, whether changes to intrinsic or extrinsic variables, can either be observed directly by the user, or indicated and directed to the user through an artificial intelligence system trained to identify optimal qualities and outcomes of a given scenario and/or user preferences.

Figure 5A:
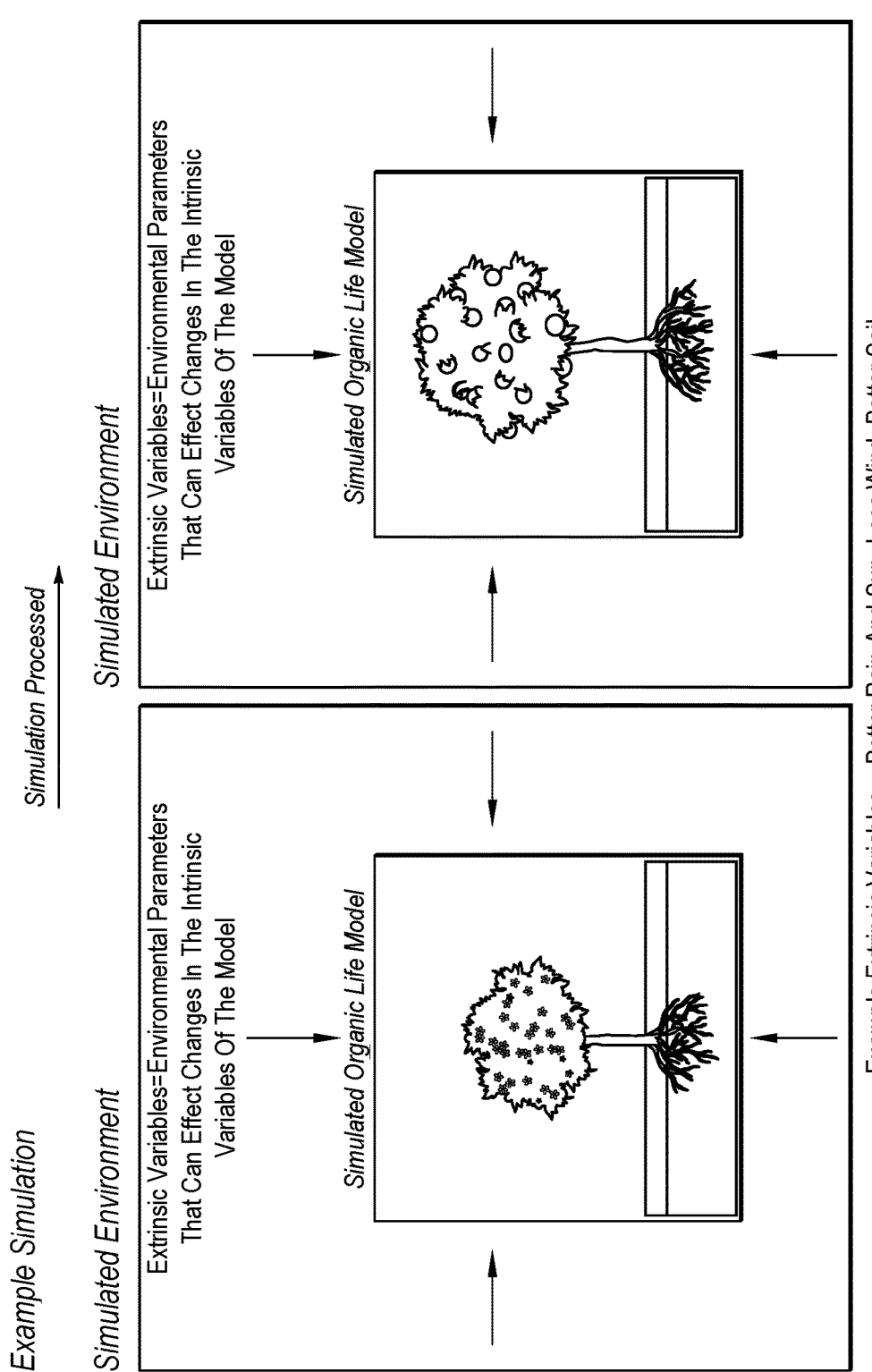
FIG. 5a is a depiction of one example embodiment of a graphical image of the simulation process.

Referring now to FIG. 5a, one example embodiment of a graphical image of the simulation process is depicted. Although the simulated organic life model is depicted as a tree, other organic selections could be chosen by a user. As the simulation proceeds from a first state to a second state, it can be seen that the simulated organic life model has grown and produced fruit. In this example, the tree has increased foliage and now has fruit. In some embodiments, this may be the result of positive extrinsic variables such as, for example, better rain and sun, less wind, and better soil. Intrinsic variables of the simulated organic life model may be changed based on the positive extrinsic variables. For example, in some embodiments, the simulated organic life model may have increased growth, larger roots, a bigger trunk, more fruit, and/or more leaves. In this example, the tree is healthier under this particular simulation and scenario.

Figure 5B:
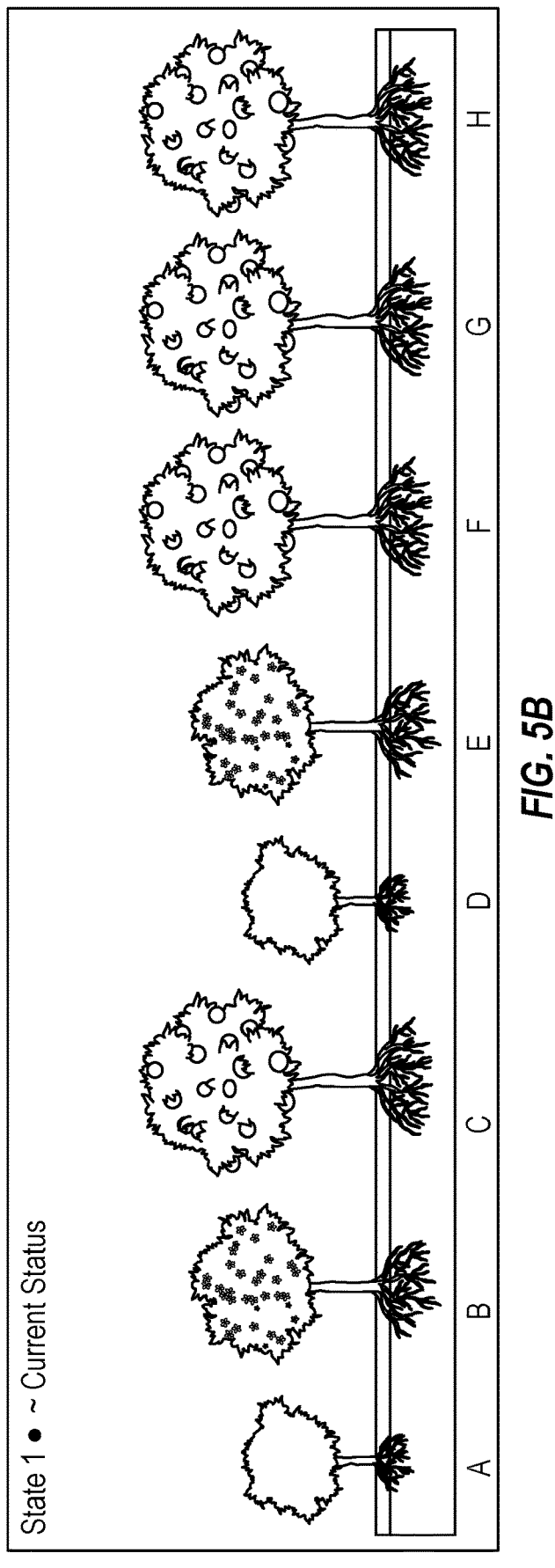
FIG. 5b is a depiction of one example embodiment of a graphical image of the simulation process for multiple simulated organic life models in an example current state.

Referring now to FIGS. 5b-5e, example embodiments of a graphical image of the simulation process for multiple simulated organic life models are depicted. Although illustrated with eight organic life models, a greater or fewer number of organic life models could be used. In addition, although some or each organic life model of the simulated environment is depicted as a tree, different organic life models may be selected for some or each simulated organic life model. In addition, different species of trees may also be selected for some or each simulated organic life model. In FIG. 5b, a State 1 may reflect the current status of some or each of the simulated organic life models. Some or each of the simulated organic life models may be at a different physical state. For example, "A" and "D" may be smaller than the other trees. "B" and "E" may be of intermediate height and may have some flowering. "C," "F," "G," and "H" may be the largest trees, may have the most extensive root systems, and may have fruit. In these and other embodiments, the physical state of a tree may be correlated with intrinsic data of the simulated organic life model and may be parsed data from an external source. For example, in some embodiments some or each tree may correlate with a different company. The physical state of the tree may be correlated with the financial state of the company.

Figure 5C:
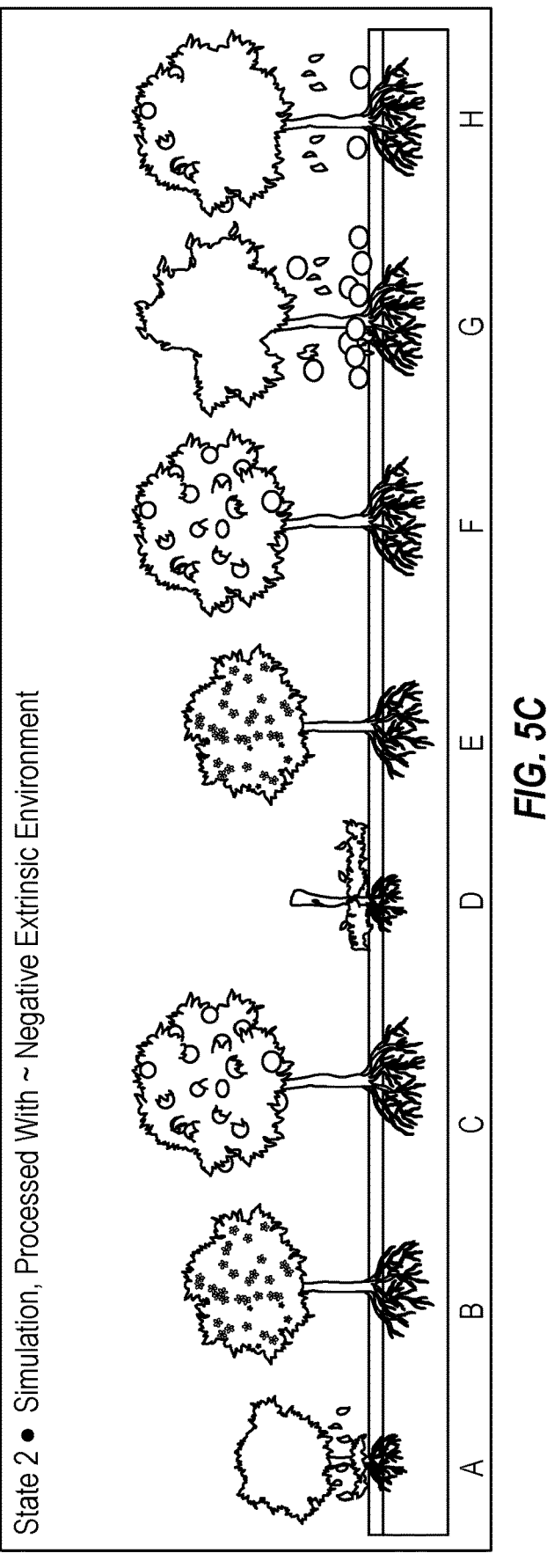
FIG. 5c is a depiction of one example embodiment of a graphical image of the simulation process for multiple simulated organic life models in an example simulation-processed state in an example negative extrinsic environment.

In FIG. 5c, State 2 may depict the results of processing the simulation with a negative extrinsic environment. As a result of processing the simulation with a negative extrinsic environment, the physical states of some or each of the trees may have changed. For example, "A" has lost some leaves and did not grow. "B," "C," "E," and "F" have not grown. "D" may have lost many or all of its leaves and may have died. "G" may have lost many leaves and much fruit. "H" may have lost some leaves and some fruit. In these and other embodiments, the physical state of a tree may be correlated with intrinsic data of the simulated organic life model and may be parsed data from an external source. For example, as a result of the negative extrinsic environment, the trees may be less healthy, may perish, or may not grow as much as it would in a neutral or positive extrinsic environment. For example, in some embodiments some or each tree may correlate with a different company. The physical state of the tree may be correlated with the financial state of the company. In a negative economic environment, the financial state of some or each company may deteriorate, stagnate, and/or grow more slowly than it would have in a positive extrinsic environment.

Figure 5D:
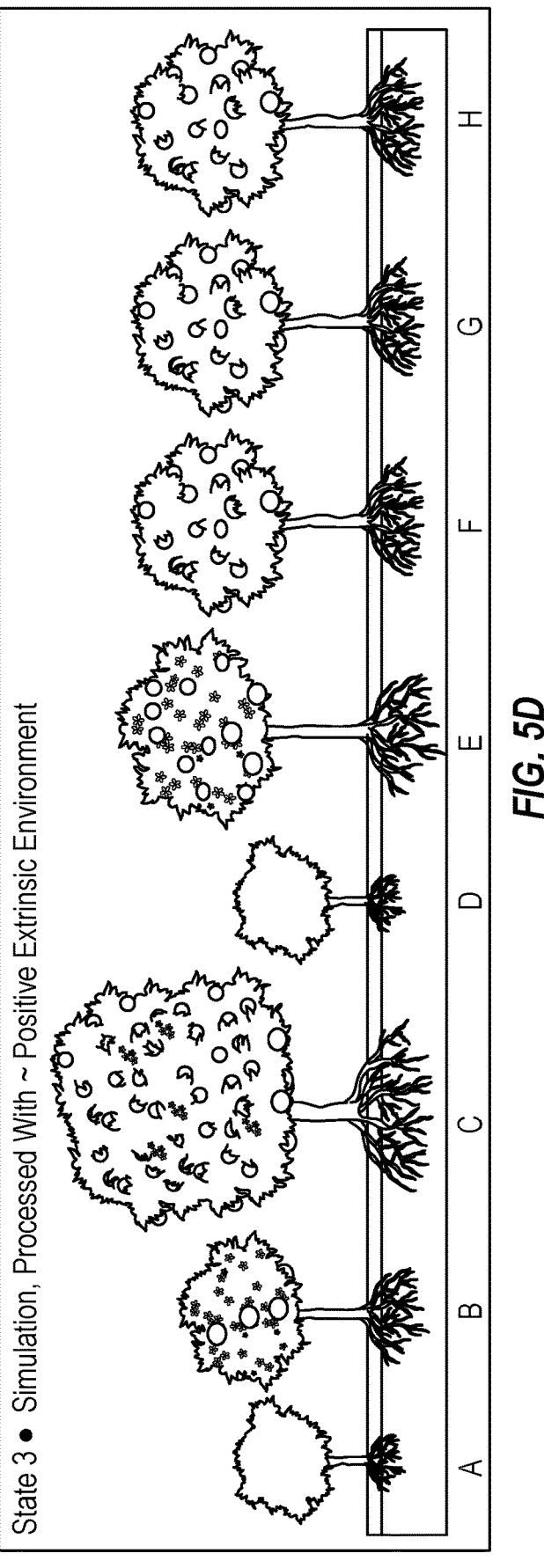
FIG. 5d is a depiction of one example embodiment of a graphical image of the simulation process for multiple simulated organic life models in an example simulation-processed state in an example positive extrinsic environment.

In FIG. 5d, State 3 may depict the results of processing the simulation with a positive extrinsic environment. As a result of processing the simulation with a positive extrinsic environment, the physical states of some or each of the trees may have changed. For example, "B" has gained a little fruit. "C" may have grown significantly and developed more extensive roots. "E" may have gained a moderate amount of fruit and grown a little. "A," "D," "F," "G," and "H" may be unchanged from their physical state in State 1. In some embodiments, however, they may have an improved physical state in comparison to their physical state in State 2. For example, "A," "D," "G," and "H" may be in a healthier physical state in State 3 than in State 2. In these and other embodiments, the physical state of a tree may be correlated with intrinsic data of the simulated organic life model and may be parsed data from an external source. For example, as a result of the positive extrinsic environment, the trees may be healthier, may have more fruit, or may grow more than in a neutral or negative extrinsic environment. For example, in some embodiments some or each tree may correlate with a different company. The physical state of the tree may be correlated with the financial state of the company. In a positive economic environment, the financial state of some or each company may improve more quickly and/or decline more slowly than it would have in a negative extrinsic environment. Additionally, in some embodiments, the graphical presentation of the trees may allow the rapid comparison of a complex data set represented by the tree. In these and other embodiments, some or each tree may represent many financial variables for a company. When presented in a tabular form, for example as shown in FIG. 5e, it may be difficult for a non-expert user to understand and/or interpret the data, but may in some cases be a desirable presentation format. By presenting the data as a simulated organic life model, a non-expert user may be able to better understand, interpret, and/or use the data to make a decision.

Additionally or alternatively, in some embodiments, changes in the model, whether changes to intrinsic or extrinsic variables, can either be observed directly by the user, or indicated and directed to the user through an artificial intelligence system trained to identify optimal qualities and outcomes of a given scenario and/or user preferences.

Figure 6A:
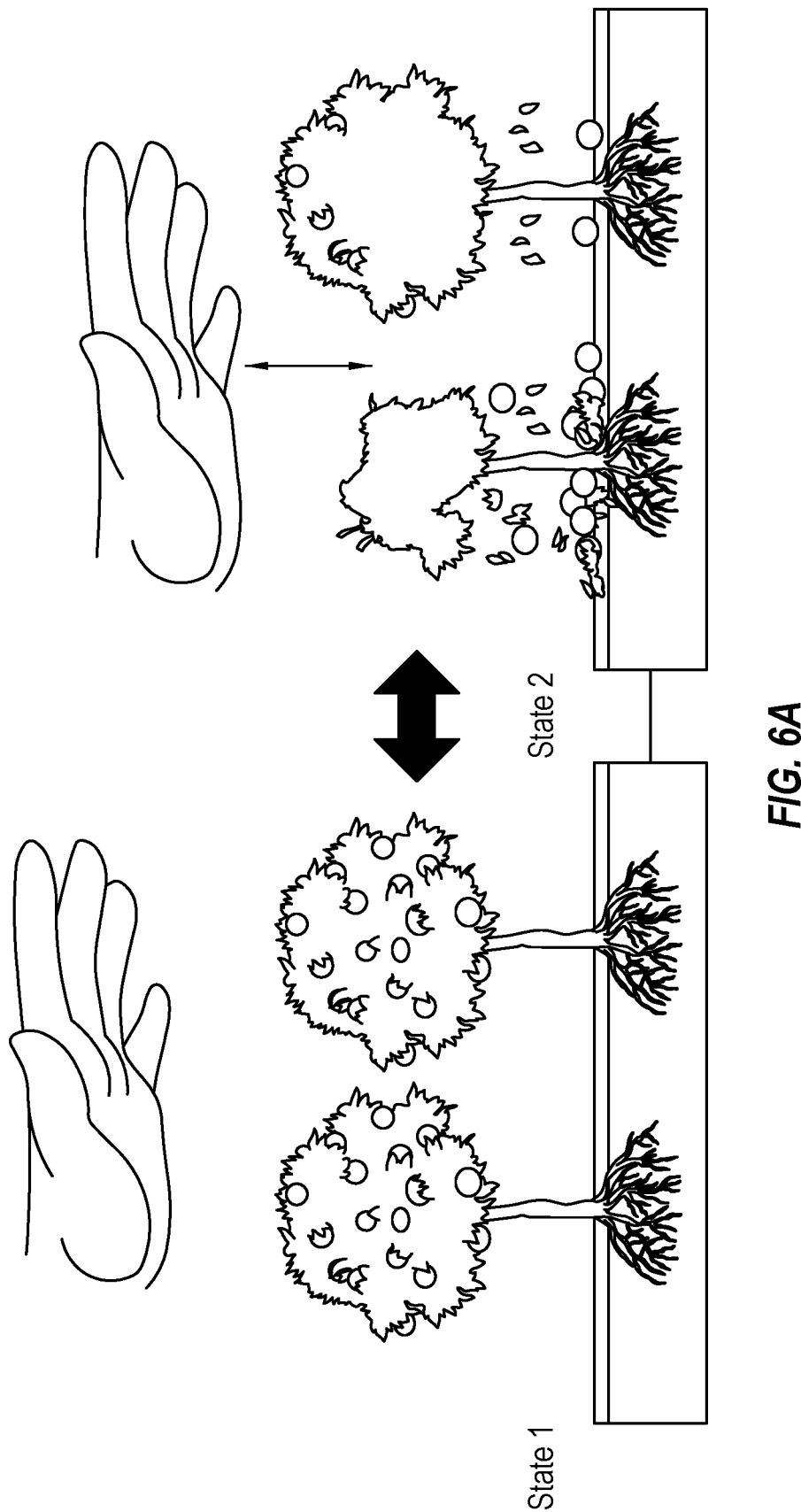
FIG. 6a is a depiction of one example embodiment of a user interacting with a simulated organic life model.

Referring now to FIG. 6a, one example embodiment of a user interacting with the simulated organic life model is depicted. In some embodiments, the user may interact with the simulated organic life model through user devices of the client system 2a of FIG. 1. For example, a user may make selections using a keyboard and/or a mouse that may cause a physical interaction with the simulated organic life models. For example, a user may choose to hit the trees, which may result in a deterioration of the health of the trees between State 1 and State 2. For example, the trees may lose leaves and fruit after the interaction by the user. In some embodiments, the user may interact with the simulation by means of a haptic device and may physically move his or her hands to interact with the simulation in a virtual reality environment.

In some embodiments, user devices or other data collecting/sensing devices can be used to alter variables within the simulation. These wired or wireless devices may include a computer keyboard, a set of switches, foot peddle switches, a mouse, tracker-ball or stylus or other pointer, gyroscopic directional sensors, biometric sensors (blood pressure, body temperature, heartbeat, ventricular pressure, blood glucose, other blood chemistry sensors), physical and chemical probes (pH, temperature, light, gravity), and any other device capable of providing a signal to a device.

In some embodiments, user devices may include haptic response devices and systems which can apply virtual forces, or variables, to the simulation as well as allow a user to receive haptic responses that can be felt by the user, describing simulation events, model shape or texture, or other forces proportional to variables in the simulation.

Figure 6B:
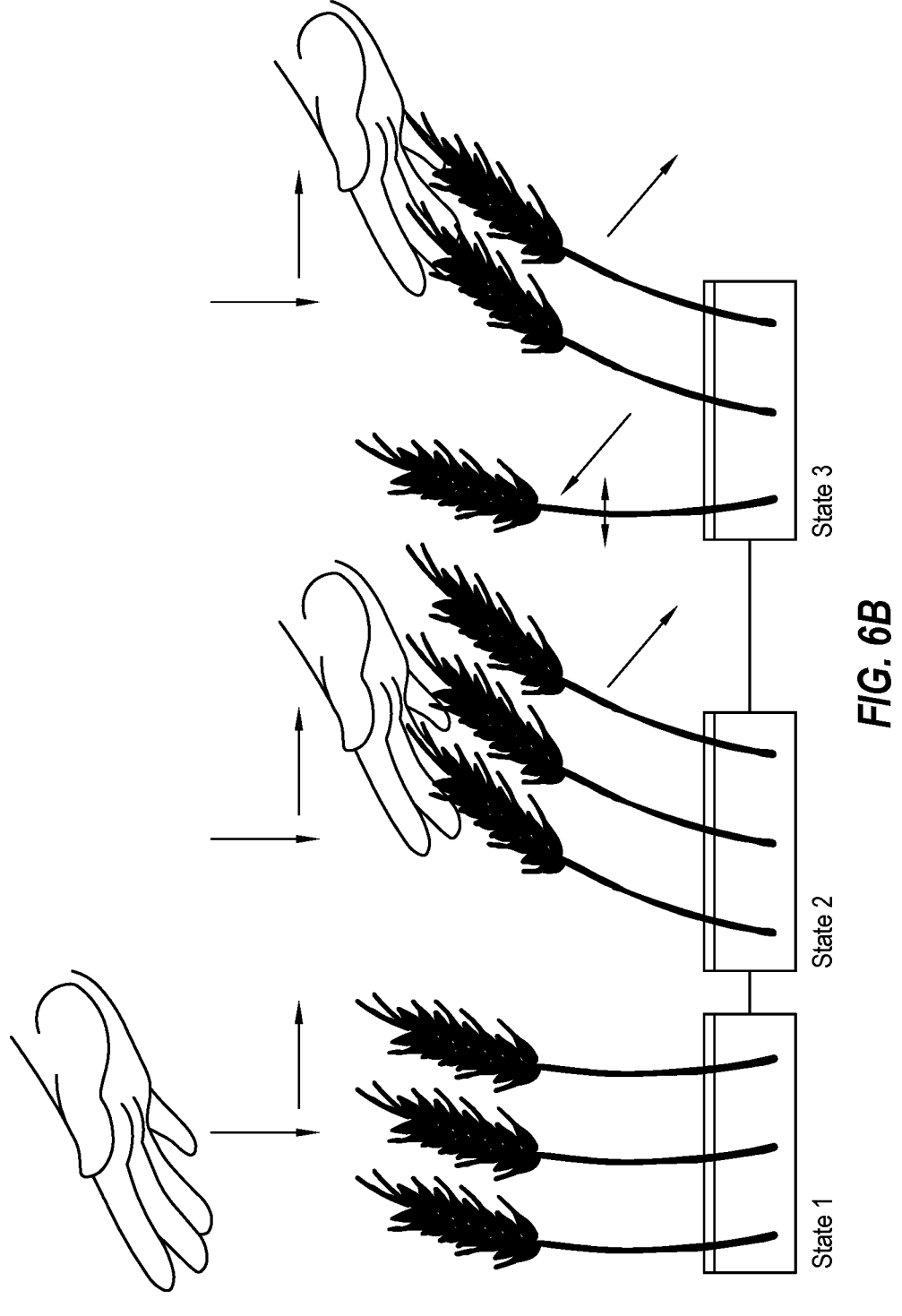
FIG. 6b is a depiction of one example embodiment of a user interacting with a simulated organic life model.

Referring now to FIG. 6b, one example embodiment of a user interacting with the simulated organic life model is depicted. In some embodiments, the user may interact with the simulated organic life model through user devices of the client system 2a of FIG. 1. For example, a user may make selections using a keyboard and/or a mouse that may cause a physical interaction with the simulated organic life models. For example, a user may choose to brush the plants, which may result in a temporary or permanent realignment of the plants between State 1, State 2, and State 3. After the user is no longer interacting with a plant, it may return to approximately the same state as it was prior to the interaction. For example, in State 3 one plant is no longer being interacted with and may return to approximately the same state as it was in State 1. The user interacting with the plants may cause the plant to lean to one side. In some embodiments, the user may interact with the simulation by means of a haptic device and may physically move his or her hands to interact with the simulation in a virtual reality environment.

Figure 6C:
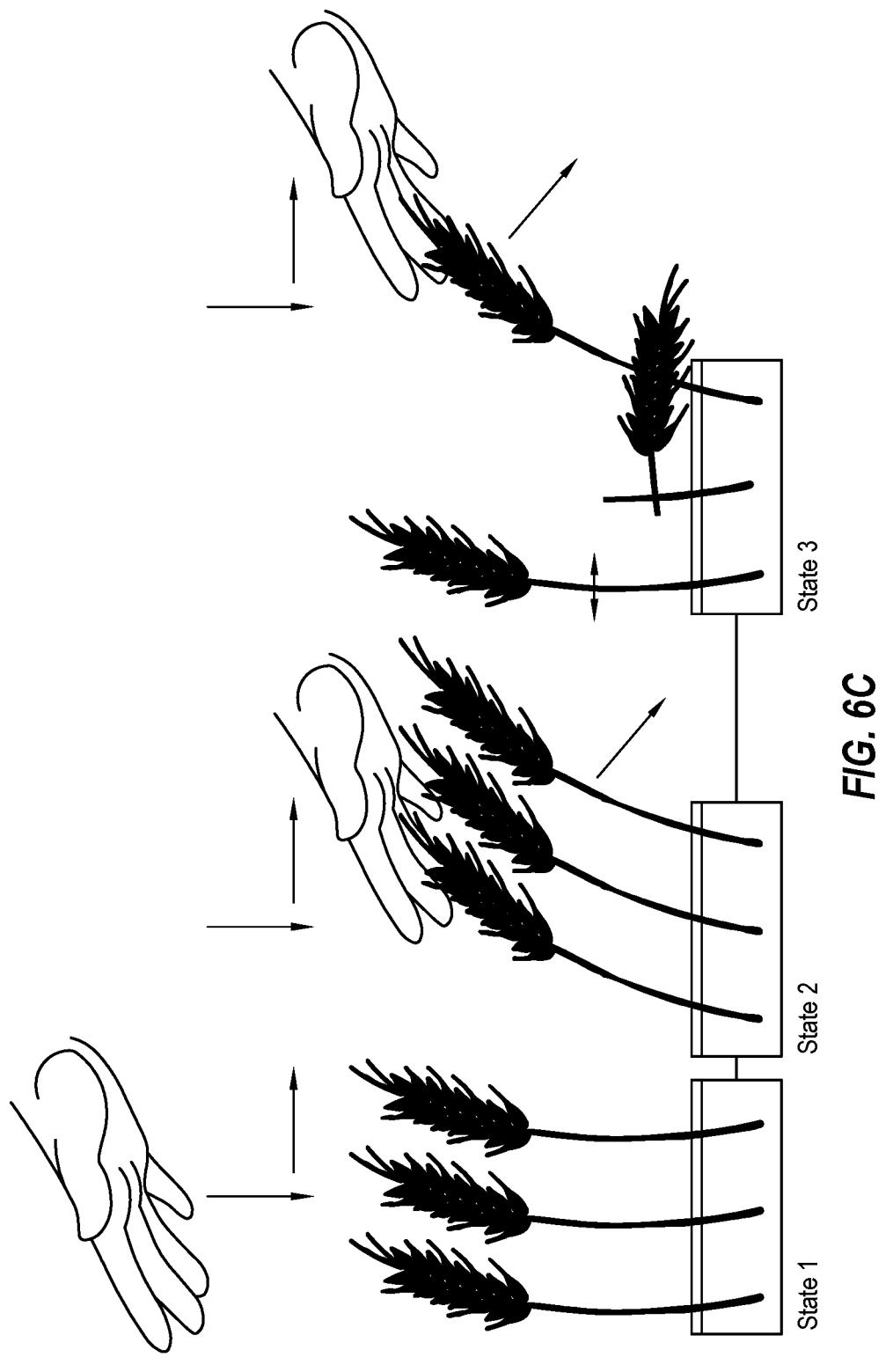
FIG. 6c is a depiction of one example embodiment of a user interacting with a simulated organic life model.

Referring now to FIG. 6c, one example embodiment of a user interacting with the simulated organic life model is depicted. In some embodiments, the user may interact with the simulated organic life model through user devices of the client system 2a of FIG. 1. For example, a user may make selections using a keyboard and/or a mouse that may cause a physical interaction with the simulated organic life models. For example, a user may choose to brush the plants, which may result in a temporary or permanent realignment of the plants between State 1, State 2, and State 3. After the user is no longer interacting with a plant, it may return to approximately the same state as it was prior to the interaction. For example, in State 3 one plant is no longer being interacted with and may return to approximately the same state as it was in State 1. Alternatively or additionally, a plant may be permanently affected by the interaction by the user. For example, a plant may be damaged or destroyed by the interaction by the user. For example, in State 3 one of the plants has been broken. The user interacting with the plants may cause the plant to lean to one side. In some embodiments, the user may interact with the simulation by means of a haptic device and may physically move his or her hands to interact with the simulation in a virtual reality environment.

Figure 7A:
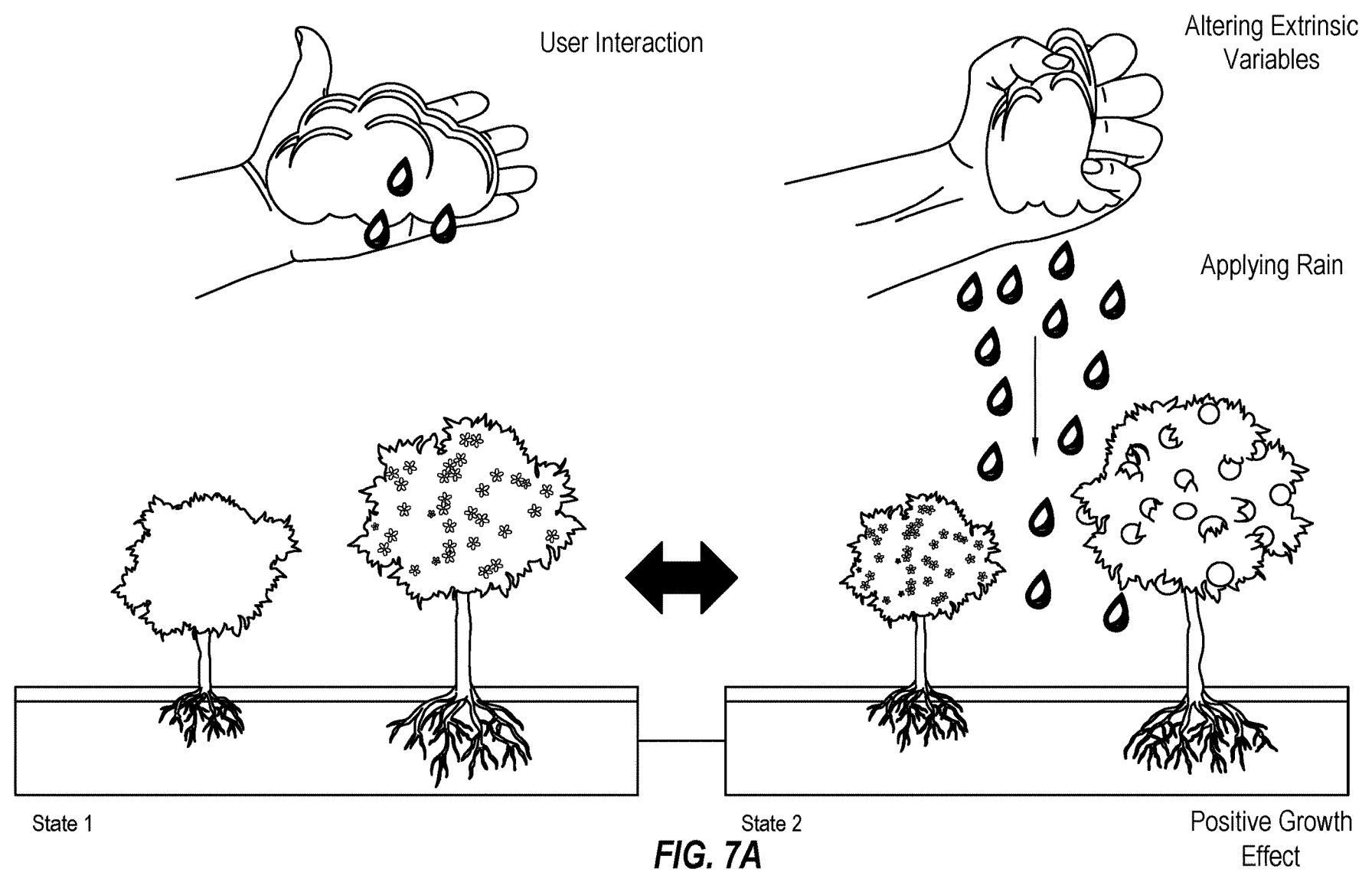

Referring now to FIG. 7a, one example embodiment of a user interacting with the simulated environment is depicted. In some embodiments, the user may interact with the simulated environment through user devices of the client system 2a of FIG. 1. For example, a user may make selections using a keyboard and/or a mouse that may cause a change in the simulated environment. For example, a user may choose to cause additional rainfall, which may result in a positive growth effect and an improvement in the health of the trees between State 1 and State 2. For example, the trees may start flowering and may bear fruit after the interaction by the user. In some embodiments, the user may interact with the simulated environment by means of a haptic device and may physically move his or her hands to interact with the simulated environment in a virtual reality environment. For example, a user may choose to squeeze a cloud, which may cause rain to fall on the simulated organic life models. Alternatively or additionally, a user may interact with clouds to increase sunlight in the simulated environment, blow on the simulated organic life models to increase the wind in the simulated environment, shake the ground to cause an earthquake, and/or interact with the simulated environment in other ways. Additionally, in some embodiments, the graphical presentation of the trees may allow the rapid comparison of beneficial outcomes in an external environment on a complex data set represented by the trees. In these and other embodiments, some or each tree may represent many financial variables for a company. When presented in a tabular, numerical, and/or chart form, it may be difficult for a non-expert user to understand, compare, and/or interpret the data. By presenting the data as a simulated organic life model, a non-expert user may be able to better understand, interpret, compare, and/or use the data to make a decision. For example, a user may be able to determine that a certain tree, representing a certain company, will experience greater growth in a certain positive external environment.

Figure 7B:
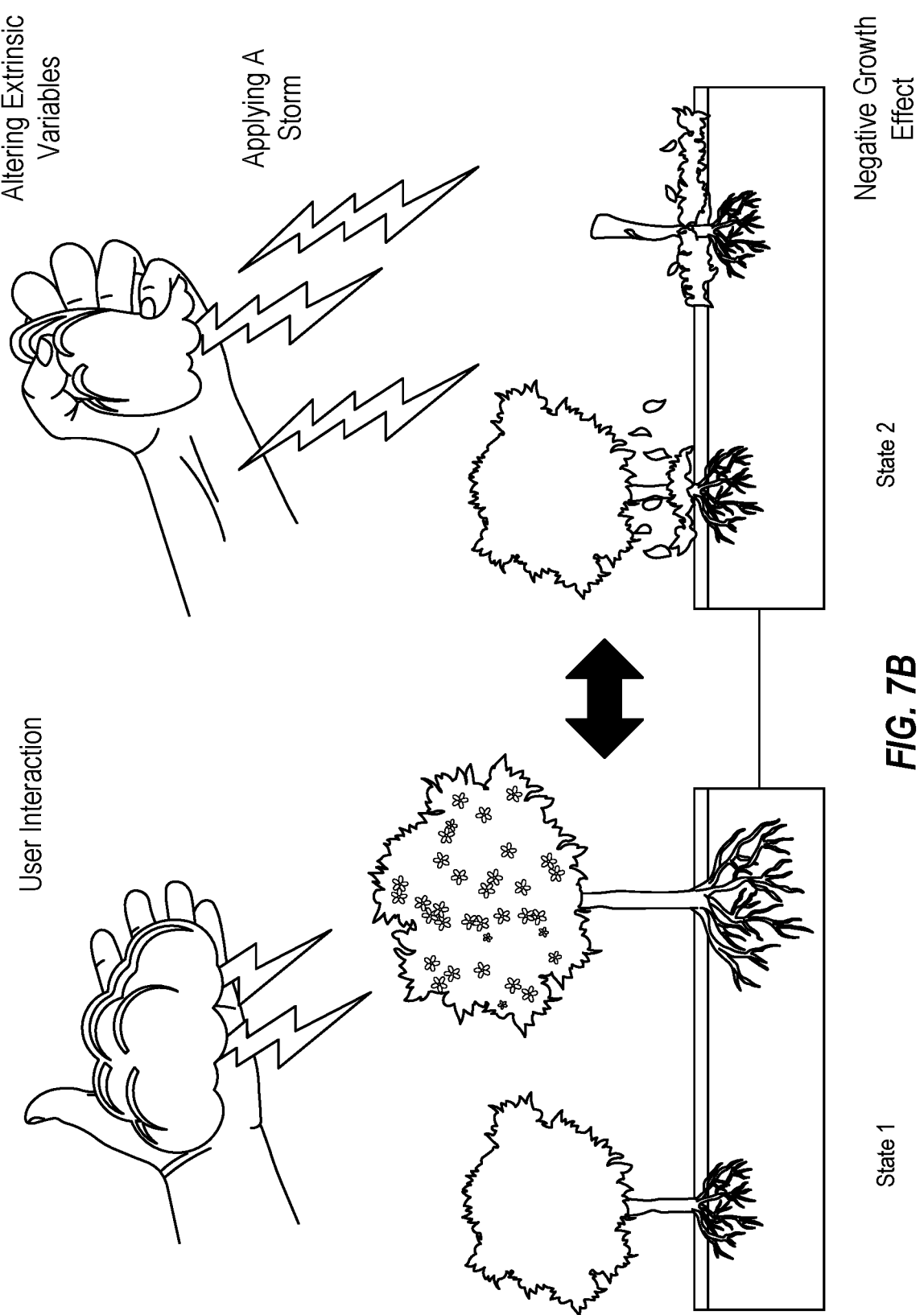
FIG. 7b is a depiction of one example embodiment of a user interacting with a simulated environment.

Referring now to FIG. 7b, one example embodiment of a user interacting with the simulated environment is depicted. In some embodiments, the user may interact with the simulated environment through user devices of the client system 2a of FIG. 1. For example, a user may make selections using a keyboard and/or a mouse that may cause a change in the simulated environment. For example, a user may choose to cause additional thunderstorms, which may result in a negative growth effect and a deterioration of the health of the trees between State 1 and State 2. For example, the trees may lose leaves and/or die after the interaction by the user. In some embodiments, the user may interact with the simulated environment by means of a haptic device and may physically move his or her hands to interact with the simulated environment in a virtual reality environment. For example, a user may choose to squeeze a storm cloud, which may cause lightning to strike the ground and/or the simulated organic life models. Additionally, in some embodiments, the graphical presentation of the trees may allow the rapid comparison of negative outcomes in an external environment on a complex data set represented by the trees. In these and other embodiments, some or each tree may represent many financial variables for a company. When presented in a tabular, numerical, and/or chart form, it may be difficult for a non-expert user to understand, compare, and/or interpret the data. By presenting the data as a simulated organic life model, a non-expert user may be able to better understand, interpret, compare, and/or use the data to make a decision. For example, a user may be able to determine that a certain tree, representing a certain company, will experience greater decline in a certain negative external environment.

Figure 7C:
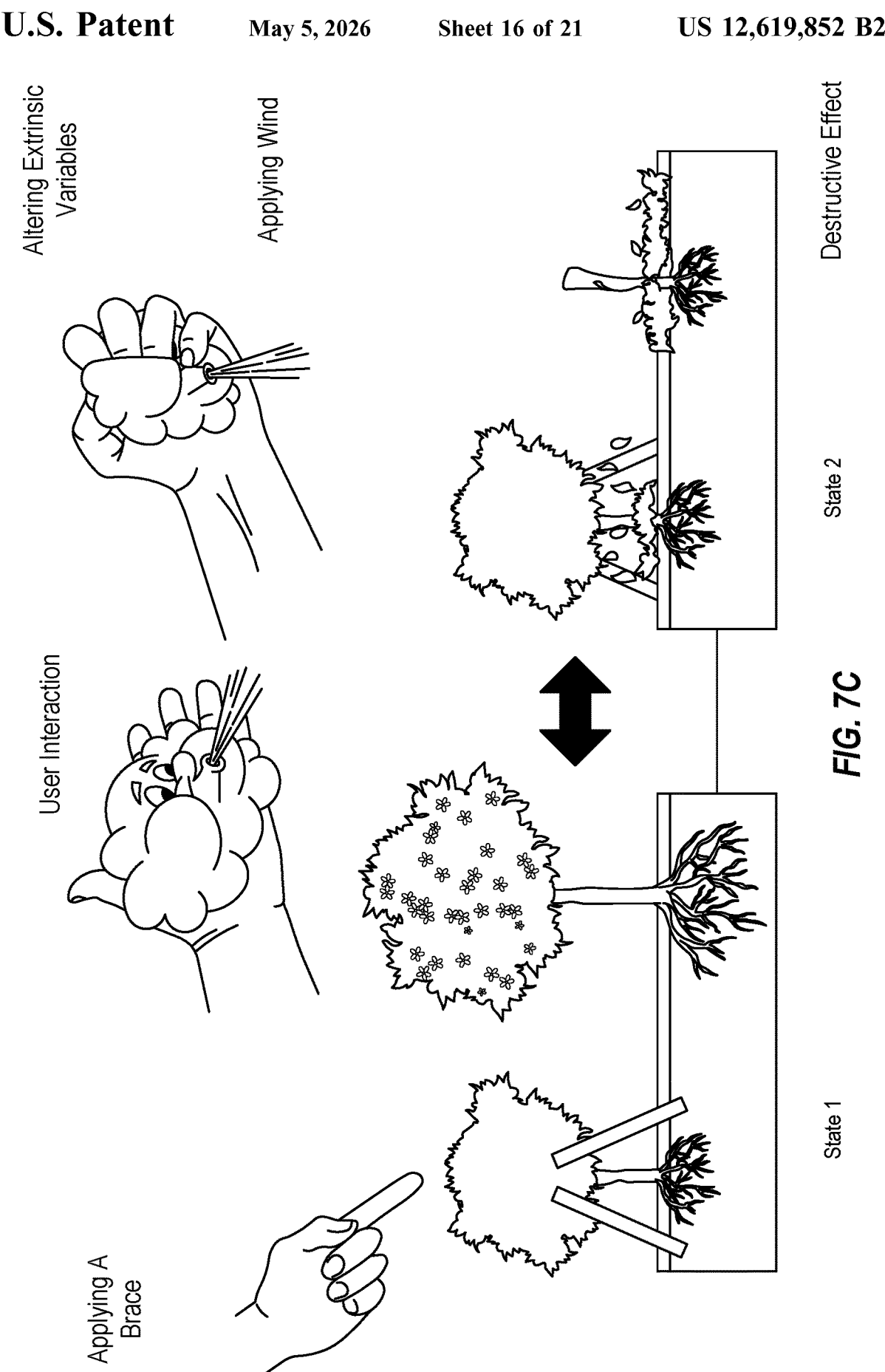
FIG. 7c is a depiction of one example embodiment of a user interacting with a simulated environment.

Referring now to FIG. 7c, one example embodiment of a user interacting with the simulated environment is depicted. In some embodiments, the user may interact with the simulated environment through user devices of the client system 2a of FIG. 1. For example, a user may make selections using a keyboard and/or a mouse that may cause a change in the simulated environment. For example, a user may choose to apply a brace to one or more trees in the simulated environment, which may reduce the destructive effect of some environmental factors on the tree, such as wind. In addition, a user may choose to cause additional wind after applying the brace, which may result in a destructive effect and a deterioration of the health of some of the trees between State 1 and State 2. For example, the trees may lose leaves and/or die after the interaction by the user. For example, the tree without the brace in State 1 may lose many or all of its leaves and die after application of the wind between State 1 and State 2. The tree with the brace may lose leaves between State 1 and State 2 but may not die. In some embodiments, the user may interact with the simulated environment by means of a haptic device and may physically move his or her hands to interact with the simulated environment in a virtual reality environment. For example, a user may choose to place support braces around one tree. Additionally or alternatively, a user may choose to squeeze a wind cloud, which may cause wind to blow the ground and/or the simulated organic life models. Additionally, in some embodiments, the graphical presentation of the trees may allow the rapid comparison of negative outcomes in an external environment on a complex data set represented by the trees. In these and other embodiments, some or each tree may represent many financial variables for a company. When presented in a tabular, numerical, and/or chart form, it may be difficult for a non-expert user to understand, compare, and/or interpret the data. By presenting the data as a simulated organic life model, a non-expert user may be able to better understand, interpret, compare, and/or use the data to make a decision. For example, a user may be able to determine that a certain tree, representing a certain company, will experience greater decline in a certain negative external environment than will a different company that is receiving support.

Referring now to FIG. 8a, an interactive virtual reality system is depicted. In some embodiments, the interactive virtual reality system may include a virtual reality headset, a computer, and a sensing glove. In some embodiments, the computer may include a haptic driver unit and a glove sensor interface to detect signals from the sensing glove. In some embodiments, the sensing glove may include haptic transducers, haptic sensors, and/or vibrotactile units.

Head mounted displays, which may include tablets and/or phones, may be able to sense motion around three axes which are controlled by a gyroscope sensor in the device. The head rotation actions may be synchronous with the rotation of the camera view in the simulation, which may bring the immersive perception to the user in real time. Meanwhile, the remote controller may be used to input the displacement of the 3D scene as well as manipulate the menu of the software configuration. Pitch is rotation around X, positive when pitching up. Yaw is rotation around Y, positive when turning left. Roll is rotation around Z, positive when tilting to the left in the XY plane.

In some embodiments, a kinetic visualization sensor may visualize and interpret body parts and their movement in three dimensions without direct contact. In some embodiments, the kinetic visualization sensor may be composed of one or more cameras and/or one or more sensors which may capture images which are analyzed directly in the computer or via an external processing unit, which in turn may send the computer appropriate data as to which body part is moving and how it is moving.

An example operation of the interactive virtual reality system is as follows. A user may put on a virtual reality headset or other virtual reality device capable of producing virtual reality images. The headset may be capable of detecting motion and/or orientation such as the orientation of a user's head with respect to pitch, yaw, and roll. The headset may display a virtual reality image of the simulated environment and the simulated organic life models. In some embodiments, the virtual reality image may also include a virtual depiction of a hand, foot, or other body part of the user. For example, the virtual reality image may include a virtual depiction of a user's hand when the user puts on a sensing glove.

In some embodiments, a user may interact with the simulated environment by means of the sensing glove. The user may see the virtual simulated object in the virtual reality display and may move his or her hand to touch the virtual simulated object. The user may receive tactile and haptic responses from the sensing glove in response to "touching" the virtual simulated object. Alternatively or additionally, the user may interact with the virtual simulated object or the virtual simulated environment by hitting, pushing, squeezing, or applying other force through the glove to objects in the virtual simulated environment. In response to the user's reaction, the virtual simulated environment may change, react, and/or update. For example, as described above with respect to FIGS. 7a-7c, the interaction by the user may damage, destroy, help, heal, or otherwise impact the simulated organic life models of the virtual simulated environment.

Figure 8B:
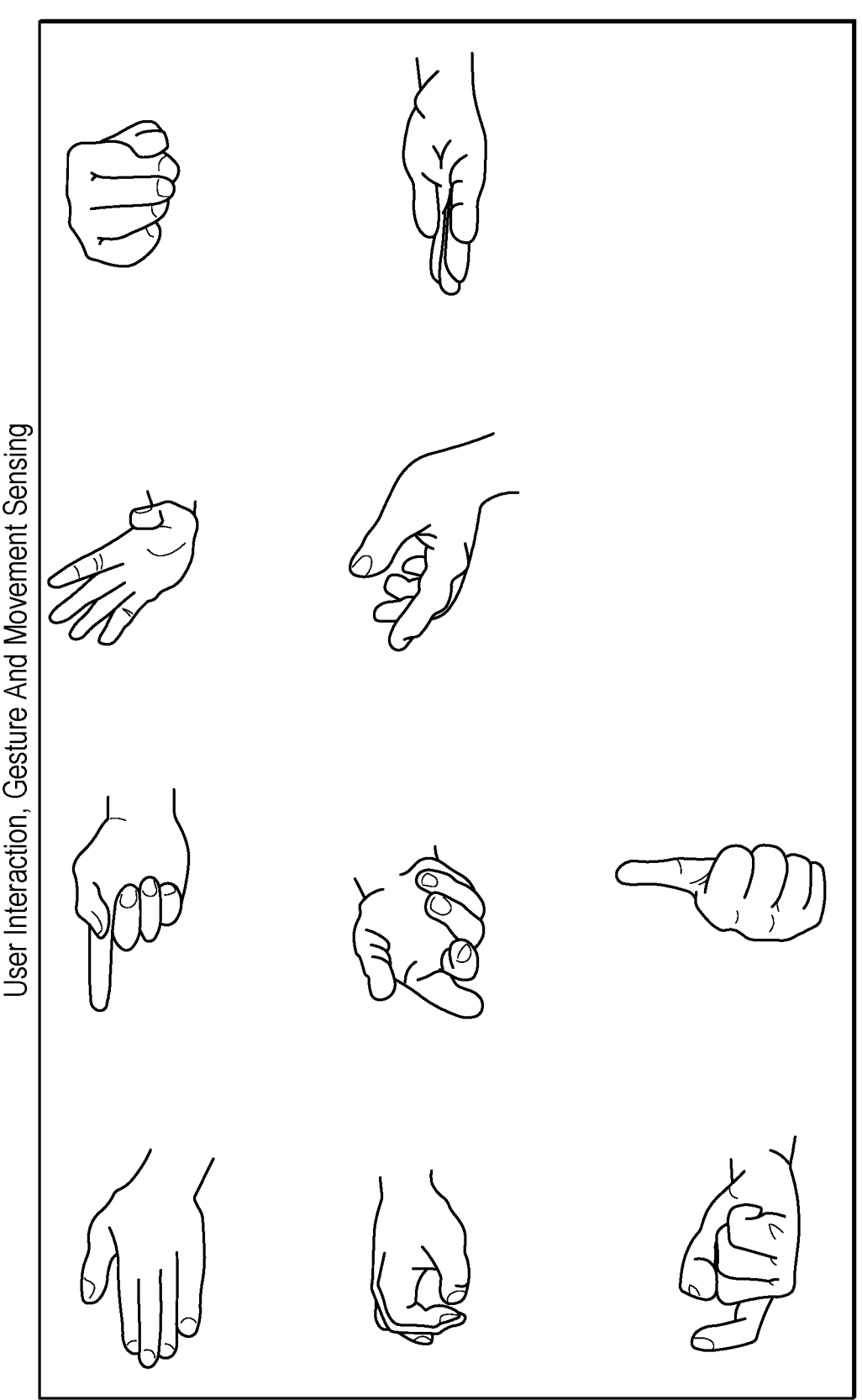
FIG. 8b is a depiction of example embodiments of user interaction, gestures, and movement sensing.

Referring now to FIG. 8b, example embodiments of user interaction, gesture, and movement sensing are depicted. A user may use a variety of gestures, interactions, and/or hand motions to interact with the virtual simulated environment.

Figure 8C:
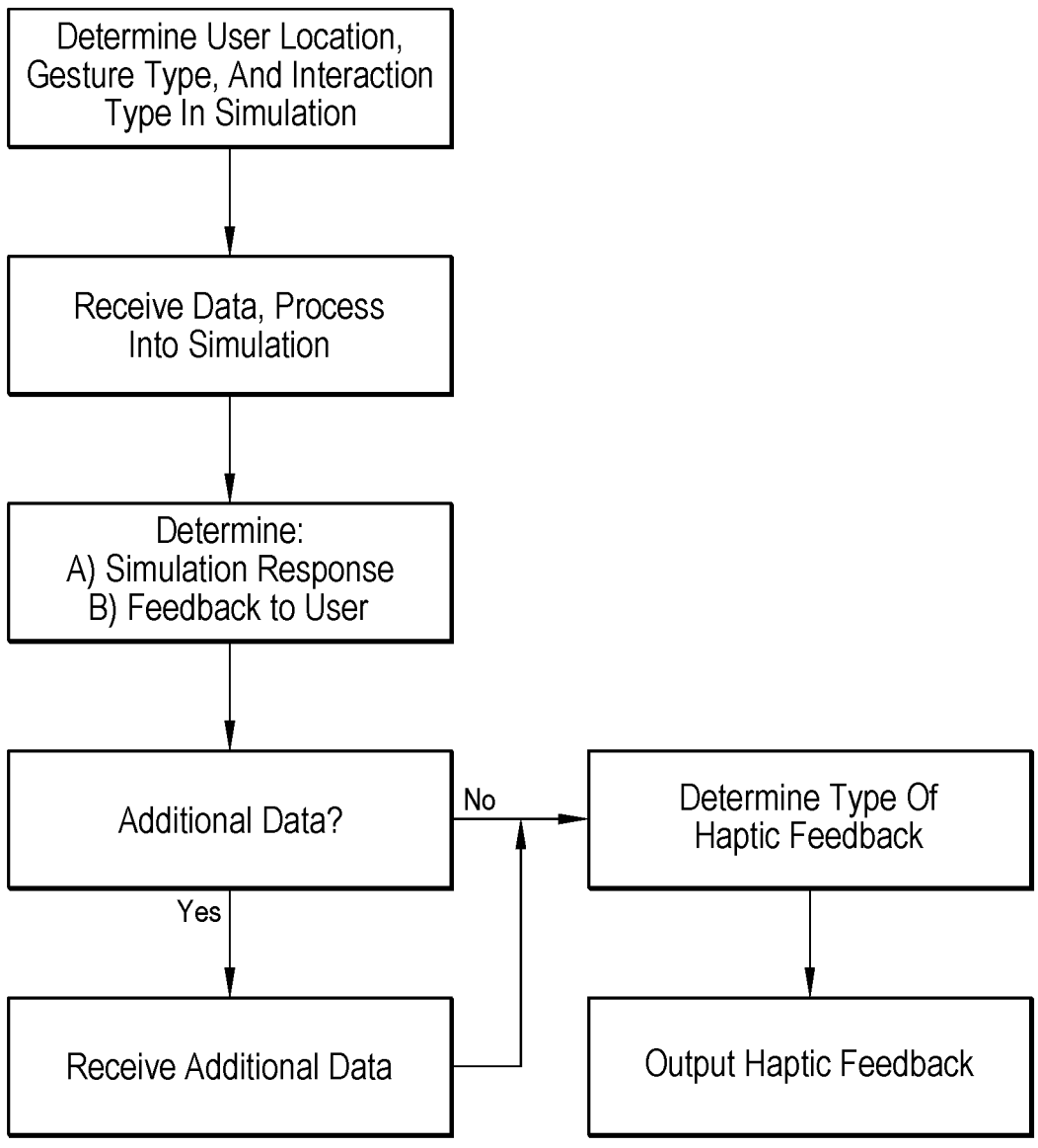
FIG. 8c is a depiction of an example method of receiving user interaction and generating haptic feedback.

Referring now to FIG. 8c, an example method of receiving user interaction and generating haptic feedback is depicted. In some embodiments, the method may begin by determining a user location, a gesture type, and an interaction type in the simulation.

The method may then receive data related to the interaction and process the data into the simulation. For example, the data may include the nature of the interaction by the user such as improving the external environment by increasing rainfall, physically interacting with a simulated organic life model to cause damage to the life model, and/or other data related to the interaction by the user.

The method may include determining the response of the simulation to the reaction and the nature of any feedback to the user. For example, the simulation response may include improved health of one or more simulated organic life models and/or deteriorated health of one or more simulated organic life models. In some embodiments, the feedback to the user may include tactile impressions from touching a simulated organic life model, haptic responses, and/or other impressions from the interaction.

In some embodiments, the method may include determining if there is additional data. In response to determining that there is additional data, the method may receive the additional data. After receiving additional data, the method may then determine the type of haptic feedback to provide to the user. In response to determining that there is no additional data, the method may then determine the type of haptic feedback to provide to the user. The type of haptic feedback that is provided to the user may be based on the user location, gesture type, interaction type, and simulation response. In some embodiments, the method may output the haptic feedback to the user. In some embodiments, the haptic feedback may be output by means of a sensing glove as discussed above with respect to FIG. 8a.

Figure 9:
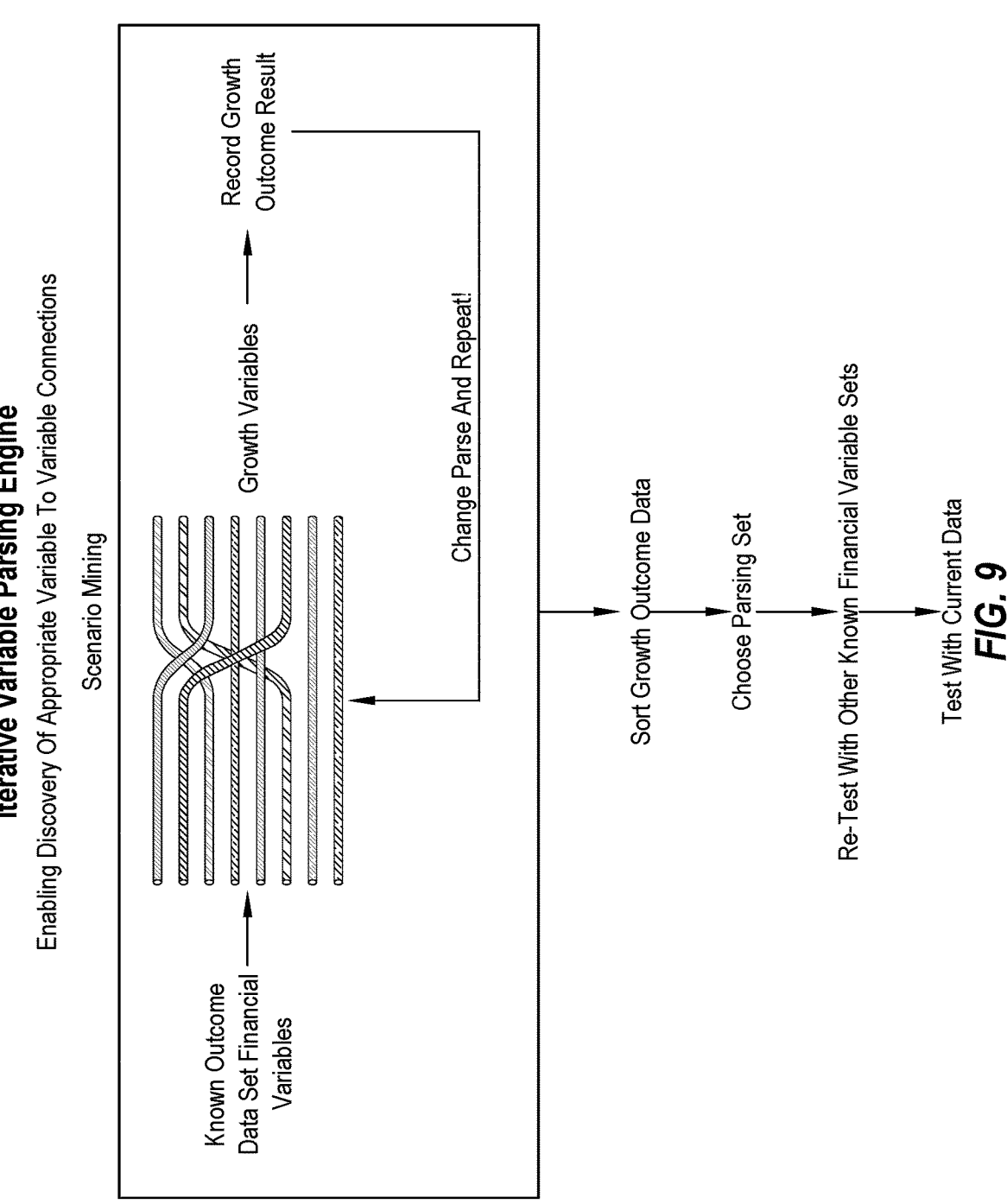
FIG. 9 is a depiction of an example embodiment of an iterative variable parsing engine.

Referring now to FIG. 9, an iterative variable parsing engine is depicted. In some embodiments, the iterative variable parsing engine may enable the discovery of an appropriate variable to variable parsing given a particular scenario, without the need to manually comprehend every variable to variable combination. In some embodiments, the iterative variable parsing engine may perform the parsing of the extrinsic and intrinsic variables from a complex data set into the simulated environment and simulated organic life models of box 6 of FIG. 2 and/or box 12 of FIG. 3. In some embodiments, the iterative variable parsing engine may receive a known outcome data set and a set of financial variables. The iterative variable parsing engine may parse the financial variables onto a set of growth variables. The iterative variable parsing engine may then process the expected growth based on the growth variables and record the outcome result. The iterative variable parsing engine may then change the parse of the financial variables onto the growth variables and repeat the process. In some embodiments, the iterative variable parsing engine may iterate through some assignment of variables, while in other embodiments every possible assignment of variables. For example, in some embodiments, the iterative variable parsing engine may factorially iterate through some number of combinations of financial variables, while in other embodiments, the iterative variable parsing engine may factorially iterate through every combination of financial variables onto a set of growth variables.

In some embodiments, the iterative variable parsing engine may choose a parsing set. In some embodiments, the iterative variable parsing engine may sort the outcome result data from some or each simulation. In some embodiments, the iterative variable parsing engine may select a parsing combination based on a desired scenario. For example, the desired scenario may be a greatest growth scenario. In this example, the iterative variable parsing engine may select the parsing that produces the greatest growth in the simulated organic life model. In some embodiments, the desired scenario may be the least growth. In these and other embodiments, the iterative variable parsing engine may select the parsing that produces the least growth in the simulated organic life model. In some embodiments, the desired scenario may include the greatest delta value in growth, the worst delta value in growth, the most fruit produced, the greatest height reached, the strongest trunk achieved, the largest root structure, and/or any desired outcome for the simulated organic life model. In some embodiments, the iterative variable parsing engine may select the variable parsing automatically, without any precise guidance to direct it regarding some or each variable, in order to obtain a desired output for a given scenario, without the need to choose or comprehend every combination of variables.

In some embodiments, the iterative variable parsing engine may re-test with other known financial variable sets. In some embodiments, by inputting known data sets with known outcomes, factorial changes in the parsing network may be applied and growth outcomes may be recorded, then sorted by delta growth/health/outcomes.

In some embodiments, the iterative variable parsing engine may test with current data to check the parsing of the iterative variable parsing engine. In some embodiments, this may occur prior to using the iterative variable parsing engine in visualizations and live simulations.

In some embodiments, in order to identify variable to variable combinations, the iterative variable parsing engine may be used to discover appropriate scenarios and appropriate parsing for a given simulation and desired outcome. In some embodiments, this could be compared to training a neural network.

Figure 10:
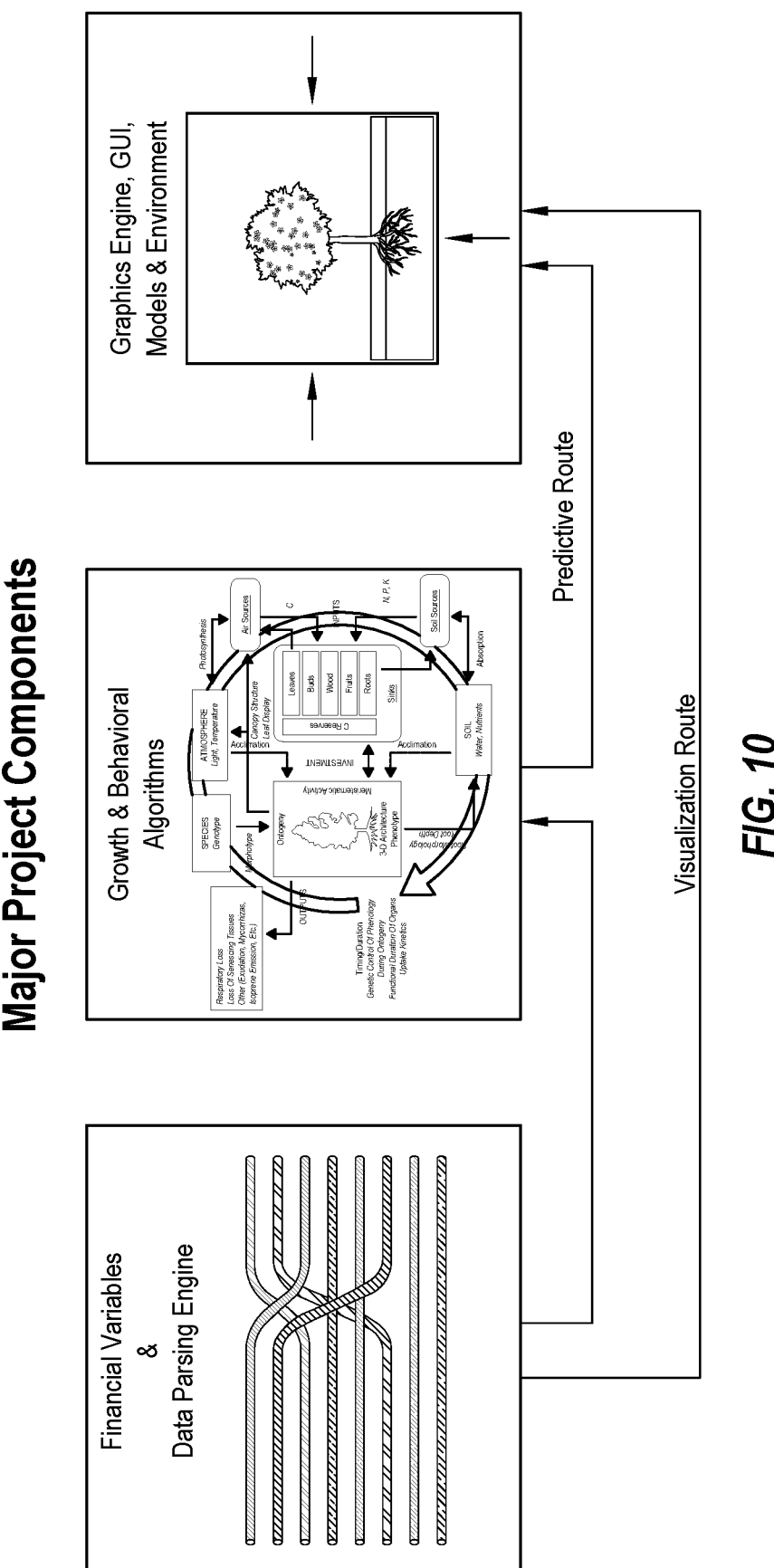
FIG. 10 is a depiction of an overview of an example simulation process.

Referring now to FIG. 10, an overview of the simulation process is depicted. In some embodiments, a variable parsing engine may generate a variable parsing that may be provided to the simulation system and to a display system. In these and other embodiments, the variable parsing engine may select a variable parsing generated by an iterative variable parsing engine, such as the iterative variable parsing engine of FIG. 9, based on a particular scenario selected by a user. Some or each variable parsing may correspond with one or more scenarios. In these and other embodiments, the parsing may correlate financial variables with growth variables of the simulated organic life model. Based on this correlation, the graphics for the models and the environment may be generated and presented to a user. In some embodiments, this may be a visualization route of the variables.

Alternately or additionally, the variable parsing engine may provide the variable parsing to the simulation system which may generate additional values for the intrinsic and extrinsic variables of the simulation based on growth and/or behavioral algorithms. The results of the growth and/or behavioral algorithms may be presented on a display in a graphical format.

A number of embodiments have been described. Nevertheless, it may be understood that various modifications may be made without departing from the spirit and scope of the invention. For example, while discussion has focused on price changes, the principals above could be applied to volume changes to depict market activity. In such a use, the values of the financial item that are used in calculations would be trading volume values and the set of threshold bands would be trading volume bands, e.g., number of shares traded over a period, e.g., a day, a week, an hour, etc. The market monitoring process would determine for the current volume of trading in the financial item a threshold trading volume band that corresponds to a current change of value in trading volume for the financial item and would select an image associated with the determined trading volume band. Accordingly, other embodiments are within the scope of the following claims.

Additionally or alternatively, in some embodiments, changes in the model, whether changes to intrinsic or extrinsic variables, can either be observed directly by the user, or indicated and directed to the user through an artificial intelligence system trained to identify optimal qualities and outcomes of a given scenario and/or user preferences.

In some embodiments, the variable parsing engine may parse the external variables to extrinsic and intrinsic variables of a battle field simulation and/or a war fighter health simulation. In these and other embodiments, a graphical depiction of a battlefield and/or a war fighter may allow a user to rapidly interpret complex data and make a logistical decision. In these and other embodiments, it may be difficult to understand the complex data set in a numeric, tabular, and/or chart form.

In some embodiments, a company may wish to know scenarios in which it can improve a certain aspect of the company's performance such as, for example, dividend payout, net income, revenue growth, etc. In some embodiments, the current variables of the company may be entered into a delta variable parsing engine. The output scenario may be more fruit. The simulation may be iteratively run, each time changing single variable amounts. By iteratively changing single variable amounts, it may be discovered that increasing a variable for bigger roots may yield more fruit. It may determine which variable in the company's data has been assigned to bigger roots. For example, in some embodiments, investment in personnel training may correspond to bigger roots. In these and other embodiments, the simulation may also change other variables that correspond to trunk size, leaf size, and/or other variables for the tree. After identification of another variable that yields more fruit, it may be determined which variable in the company's data has been assigned to that variable. For example, it may be personnel reduction. In some embodiments, the simulation model may be an interactive model. In these and other embodiments, a user may be able to trim leaves, trim branches, pick fruit, and/or perform other modifications on the simulated organic life model and/or the simulated environment. In some embodiments, the simulation may be processed after such interactions.

In some embodiments, a greenhouse may be simulated. For example, for a startup company, a user may choose to simulate the startup as a seedling growing from a seed. In some embodiments, parsing the complex data set onto a greenhouse may help a user pick the right startup to invest in. In these and other embodiments, because a greenhouse may be a static environment, growth and fruit bearing of the seedling may be dependent on risk, return on investment, experience of company officers, initial investment, social media attention, media attention, intellectual property protection, etc. In these and other embodiments, these variables may be parsed into the variables of a seed growth simulation. In these and other embodiments, the scenarios may include high risk vs high gain, low risk and moderate gain, among others.

In some embodiments, the simulation may be used for individual projects within a company. In these and other embodiments, the simulation may help a user determine which project will yield the most profit with the least risk, which may be graphically shown in some embodiments as the difference between a tree that produces fruit and one that falls over in the wind.

In some embodiments, a user may select a scenario and a set of companies upon which to run the simulation. For example, a user may select "best companies for option trading today" as the scenario. The variable parsing engine may be performed to identify a variable parsing for the scenario with the company intrinsic and extrinsic data. Continuing this example, the user may select one or more currently traded stocks for the simulation. Alternatively or additionally, the user may select one or more stocks in a market and/or a subgroup of stocks that may be identified by the user. The user may process the simulation when the user desires to. The stocks that meet the scenario criteria ("best companies for option trading today") may be presented to the user and may be ranked by some characteristic of the stocks, such as market capitalization, enterprise value, risk, and/or other risk, valuation, or other parameters of the stock.

The term "substantially" means within 5% or 10% of the value referred to or within manufacturing tolerances.

Various embodiments are disclosed. The various embodiments may be partially or completely combined to produce other embodiments.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Some portions are presented in terms of algorithms or symbolic representations of operations on data bits or binary digital signals stored within a computing system memory, such as a computer memory. These algorithmic descriptions or representations are examples of techniques used by those of ordinary skill in the data processing art to convey the substance of their work to others skilled in the art. An algorithm is a self-consistent sequence of operations or similar processing leading to a desired result. In this context, operations or processing involves physical manipulation of physical quantities. Typically, although not necessarily, such quantities may take the form of electrical or magnetic signals capable of being stored, transferred, combined, compared, or otherwise manipulated. It has proven convenient at times, principally for reasons of common usage, to refer to such signals as bits, data, values, elements, symbols, characters, terms, numbers, numerals, or the like. It should be understood, however, that all of these and similar terms are to be associated with appropriate physical quantities and are merely convenient labels. Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical, electronic, or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general-purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

While the present subject matter has been described in detail with respect to specific embodiments thereof, it will be appreciated that those skilled in the art, upon attaining an understanding of the foregoing, may readily produce alterations to, variations of, and equivalents to such embodiments. Accordingly, it should be understood that the present disclosure has been presented for-purposes of example rather than limitation, and does not preclude inclusion of such modifications, variations, and/or additions to the present subject matter as would be readily apparent to one of ordinary skill in the art.

That which is claimed:

1. A method of handling data, the method comprising:
   receiving a data stream of data comprising a plurality of variables, wherein the plurality of variables includes a first variable describing a characteristic of a company and a second variable describing a characteristic of an environment of the company;
   assigning each variable of the plurality of variables in the data stream to a respective variable of a simulated organic life model or a simulated environment, such that the first variable is assigned to a variable representing a physical parameter of a simulated organic life model and the second variable is assigned to a variable of the simulated environment, wherein the simulated organic life model represents the company as an organism modeled by the simulated organic life model, the organism being a plant, tree, fern, coral, fish, anemone, or animal;
   processing a simulation of the simulated organic life model in the simulated environment based on the assigned first variable and second variable, wherein the simulation simulates a biological process of the organism persisting, growing, adapting, sustaining damage, flourishing, or dying in the simulated environment based on a simulated effect of the variable of the simulated environment on the organism, and the simulation generates a visual representation of the organism such that a visual appearance of the organism represents a state of the company;
   altering one or more variables of the simulated organic life model based on one or more variables of the simulated environment;
   producing output data sets containing data from the data stream to predicted endpoint values for each data stream variable; and
   changing the simulated organic life model based on the altered one or more variables of the simulated organic life model;
   wherein the changing of the simulated organic life model changes the visual appearance of the organism in the simulation.

2. The method of claim 1, wherein the simulated organic life model includes intrinsic variables configured as one or more outputs indicating physical parameters or physical characteristics.

3. The method of claim 1, wherein the simulated environment simulates a mountain, a farm, plains, a celestial environment, a forest, a river, a desert, an atmospheric environment, or an aquatic environment.

4. The method of claim 3, wherein the simulated environment includes extrinsic variables configured as one or more inputs or environmental parameters to affect changes in the simulated organic life model.

5. The method of claim 1, wherein the data corresponds to economic markets, security systems, employment systems, national systems, weapons systems, or health management systems.

6. The method of claim 1, wherein altering the one or more variables of the simulated organic life model includes, in response to the processing the simulation of the simulated organic life model in the simulated environment based on the one or more variables, affecting an ability of the organic life model to persist, grow, adapt, sustain damage, flourish, or die.

7. The method of claim 6, further comprising determining a possible outcome in reality, and wherein altering the organic life model's ability to persist, grow, adapt, sustain damage, flourish, or die corresponds to the possible outcome.

8. The method of claim 7, in response to determining the possible outcome in reality, performing outside of the simulation an affirmative act, a passive act, or an act of omission, each of which corresponds to at least one variable of the data stream parsed into one or both of the simulated organic life model and the simulated environment.

9. The method of claim 1, further comprising receiving user interaction with the simulated environment.

10. The method of claim 9, wherein receiving the user interaction with the simulated environment includes receiving, from a haptic device, user interaction input through the haptic device.

11. The method of claim 9, wherein receiving the user interaction with the simulated environment includes receiving, from a virtual reality system, user interaction input through the virtual reality system.

12. A method of discovering variable to variable parsing strategies between a data stream of data and a simulated organic life model and its simulated environment, the method comprising:

receiving a data stream of data comprising a plurality of variables, wherein the plurality of variables includes a first variable describing a characteristic of a company and a second variable describing a characteristic of an environment of the company;

iteratively, for each combination of variables of the data stream and variables of the simulated organic life model and the simulated environment:

assigning each variable of the plurality of variables of the data stream to a respective variable of a simulated organic life model or a simulated environment, such that the first variable is assigned to a variable representing a physical parameter of the simulated organic life model and the second variable is assigned to a variable of the simulated environment, wherein the simulated organic life model represents the company as an organism modeled by the simulated organic life model, the organism being a plant, tree, fern, coral, fish, anemone, or animal;

processing a simulation of the simulated organic life model in the simulated environment based on the assigned first variable and second variable, wherein the simulation simulates a biological process of the organism persisting, growing, adapting, sustaining damage, flourishing, or dying in the simulated environment based on a simulated effect of the variable of the simulated environment on the organism, and the simulation generates a visual representation of the organism such that a visual appearance of the organism represents a state of the company; and recording a result of processing the simulation and a listing of each variable of the data stream and a corresponding variable of the simulated organic life model or a corresponding variable of the simulated environment;

sorting results from the processed simulations by rank order;

selecting a listing of each variable of the data stream and the corresponding variable of the simulated organic life model or the corresponding variable of the simulated environment based on the sorting; and using the listing with a different data stream of data for a chosen preferred simulation outcome;

wherein changing the simulated organic life model changes the visual appearance of the biological organism in the simulation.

13. The method of claim 12, wherein the simulated organic life model includes intrinsic variables configured as one or more outputs indicating physical parameters or physical characteristics.

14. The method of claim 12, wherein the simulated environment simulates a mountain, a farm, plains, a celestial environment, a forest, a river, a desert, an atmospheric environment, or an aquatic environment.

15. The method of claim 14, wherein the simulated environment includes extrinsic variables configured as one or more inputs or environmental parameters to affect changes in the simulated organic life model.

16. The method of claim 12, wherein the data corresponds to economic markets, security systems, employment systems, national systems, weapons systems, or health management systems.

17. The method of claim 12, wherein sorting by rank order includes sorting the results from the processed simulations according to a delta in growth, health, or outcome.

18. The method of claim 17, further comprising displaying the results in a graphical format.

* * * * *